US011629330B2

(12) United States Patent
Moreno et al.

(10) Patent No.: US 11,629,330 B2
(45) Date of Patent: Apr. 18, 2023

(54) METHOD FOR IMPROVED SPERM CELL POPULATIONS

(71) Applicant: Inguran, LLC, Navasota, TX (US)

(72) Inventors: Juan Moreno, College Station, TX (US); Kenneth Michael Evans, College Station, TX (US); Ramakrishnan Vishwanath, Hamilton (NZ); Clara Gonzalez-Marin, College Station, TX (US)

(73) Assignee: Inguran, LLC, Navasota, TX (US)

( * ) Notice: Subject to any disclaimer, the term of this patent is extended or adjusted under 35 U.S.C. 154(b) by 545 days.

(21) Appl. No.: 16/823,001

(22) Filed: Mar. 18, 2020

(65) Prior Publication Data

US 2020/0299640 A1 Sep. 24, 2020

Related U.S. Application Data

(60) Provisional application No. 62/820,724, filed on Mar. 19, 2019.

(51) Int. Cl.
| | |
|---|---|
| *C12N 5/076* | (2010.01) |
| *C12N 13/00* | (2006.01) |
| *G01N 1/30* | (2006.01) |
| *G01N 33/58* | (2006.01) |

(52) U.S. Cl.
CPC ............ *C12N 5/061* (2013.01); *C12N 13/00* (2013.01); *G01N 1/30* (2013.01); *G01N 33/582* (2013.01)

(58) Field of Classification Search
None
See application file for complete search history.

(56) References Cited

U.S. PATENT DOCUMENTS

| | | | |
|---|---|---|---|
| 5,135,759 A | 8/1992 | Johnson | |
| 5,985,216 A | 11/1999 | Rens | |
| 5,990,479 A | 11/1999 | Weiss et al. | |
| 5,998,140 A | 12/1999 | Dervan et al. | |
| 6,071,689 A | 6/2000 | Seidel | |
| 6,090,947 A | 7/2000 | Dervan et al. | |
| 6,143,901 A | 11/2000 | Dervan | |
| 6,149,867 A | 11/2000 | Seidel | |
| 6,207,392 B1 | 3/2001 | Weiss et al. | |
| 6,247,323 B1 | 6/2001 | Maeda | |
| 6,263,745 B1 | 7/2001 | Buchanan et al. | |
| 6,322,901 B1 | 11/2001 | Bawendi et al. | |
| 6,326,144 B1 | 12/2001 | Bawendi et al. | |
| 6,357,307 B2 | 3/2002 | Buchanan et al. | |
| 6,423,551 B1 | 7/2002 | Weiss et al. | |
| 6,576,291 B2 | 6/2003 | Bawendi et al. | |
| 9,804,153 B2 | 10/2017 | Krug | |
| 2001/0002314 A1 | 5/2001 | Dervan et al. | |
| 2003/0113765 A1 | 6/2003 | Dempcy et al. | |
| 2011/0143389 A1* | 6/2011 | Sharpe | G01N 15/147 435/29 |
| 2012/0270204 A1 | 10/2012 | Fox et al. | |
| 2019/0040356 A1* | 2/2019 | Durack | C12Q 1/02 |

FOREIGN PATENT DOCUMENTS

| | | |
|---|---|---|
| WO | 99/33956 A1 | 7/1999 |
| WO | 01/37655 A1 | 5/2001 |
| WO | 02/41906 A2 | 5/2002 |
| WO | 2004/088283 A2 | 10/2004 |

OTHER PUBLICATIONS

International Search Report and Written Opinion dated Jun. 17, 2020 in related PCT Appl. No.: PCT/US20/23380.
Wilson, D.E. and Reeder, D.M., Mammal Species of the World, Smithsonian Institution Press, (1993).
Best et al., "Nuclear localization of pyrrole-imidazole polyamide-fluorescein conjugates in cell culture" Proc. Natl. Acad. Sci. USA, 15 100(21): 12063-12068 (2003).
Gygi, et al., "Use of fluorescent sequence-specific polyamides to discriminate human chromosomes by microscopy and flow cytometry." Nucleic Acids Res., 30(13): 2790-2799 (2002).
Extended European Search Report dated Nov. 6, 2022 in related EP Appl. No. 20774123.2.
Canadian Office Action dated Oct. 11, 2022 in related CA Appl. No. 3,133,622.

* cited by examiner

*Primary Examiner* — Nghi V Nguyen
(74) *Attorney, Agent, or Firm* — Ryan Christensen; Hashim Rahman

(57) ABSTRACT

The invention encompasses methods for reducing the proportion of sperm cells with abnormal morphology, and unviable sperm cells, in a sperm cell population.

6 Claims, 21 Drawing Sheets

Gate A: 0 Degrees

Gate B: 45 Degrees

Gate C: 90 Degrees

METHOD FOR IMPROVED SPERM CELL POPULATIONS

REFERENCE TO RELATED APPLICATIONS

This application claims the benefit of U.S. Provisional Patent Application No. 62/820,724 filed Mar. 19, 2019. The entire disclosure of which is incorporated herein by reference.

BACKGROUND OF THE INVENTION

Limited quantities of gametes, such as sperm and oocytes, from animals of the highest genetic merit or of elite genomic value can reduce the capacity for genetic dissemination and genetic improvement within a species. As such, there is a need within the animal breeding industry, and in particular the livestock industry, for maximizing the efficiency in the use of such gametes.

SUMMARY OF THE INVENTION

One embodiment of the invention comprises a method of processing sperm cells comprising: a) selecting a population of sperm cells wherein greater than 25% of sperm cells in the population have abnormal morphology; b) staining the sperm cells in the population; c) irradiating the sperm cells in the population; d) detecting fluorescence emitted by the sperm cells in the population in response to the step of irradiating; e) differentiating the sperm cells in the population based on orientation or viability; and f) collecting a subpopulation of oriented or viable sperm cells, wherein 85% or less of the sperm cells in the collected subpopulation bear an X-chromosome or 85% or less of the sperm cells in the collected subpopulation bear an Y-chromosome. In a particular embodiment, the percentage of sperm cells in the collected subpopulation having abnormal morphology is less than the percentage of sperm cells in the population having abnormal morphology in step a). In a further embodiment, in step e), the sperm cells are differentiated based on orientation and viability. In an even further embodiment, the method further comprises the step of staining the population of sperm cells with a quenching dye. In a particular embodiment, greater than 25% of sperm cells in the population have abnormal head morphology. In another embodiment, greater than 30% of sperm cells in the population have abnormal tail morphology. In yet another embodiment, greater than 35% of sperm cells in the population have abnormal morphology. In an additional embodiment, in step b) the sperm cells are stained with a DNA-selective dye. In a particular embodiment, the DNA-selective dye is Hoechst 33342. In another embodiment, the method further comprises the step of contacting the sperm cells in the population with magnetic particles. In certain embodiments, the step of differentiating the sperm cells in the population comprises creating a gated region based on the detected fluorescence emitted by the sperm cells in the population, wherein the gated region encompasses oriented or viable sperm cells. In other embodiments, the step of differentiating the sperm cells in the population comprises creating a gated region that excludes quenched, dead sperm and sperm having a higher incidence of abnormal morphology, and collecting sperm within the gated region.

Another embodiment of the invention comprises a method of processing sperm cells comprising: a) selecting a population of sperm cells wherein greater than 45% of sperm cells in the population have abnormal morphology; b) staining the sperm cells in the population; c) irradiating the sperm cells in the population; d) detecting fluorescence emitted by the sperm cells in the population in response to the step of irradiating; e) differentiating the sperm cells in the population based on orientation or viability; and f) collecting a subpopulation of oriented or viable sperm cells, wherein the percentage of sperm cells in the subpopulation having abnormal morphology is at least 50% lower than the percentage of sperm cells in the population having abnormal morphology in step a).

An additional embodiment of the invention comprises a method of processing sperm cells comprising: a) selecting a population of sperm cells wherein greater than 25% of sperm cells in the population have abnormal morphology; b) contacting the population of sperm cells with magnetic particles; c) staining the sperm cells in the population; d) irradiating the sperm cells in the population; e) detecting fluorescence emitted by the sperm cells in the population in response to the step of irradiating; f) differentiating the sperm cells in the population based on orientation or viability; and g) collecting a subpopulation of oriented or viable sperm cells. In a particular embodiment, the magnetic particles bind to dead or damaged sperm cells in the population through an electrical charge interaction. In a further embodiment, 90% or more of the sperm cells in the collected subpopulation bear an X-chromosome or 90% or more of the sperm cells in the collected subpopulation bear a Y-chromosome, and 15% or less of the sperm cells in the collected subpopulation have abnormal morphology.

One more embodiment of the invention comprises a method of processing a population of sperm cells having abnormal morphology comprising: a) selecting a population of sperm cells wherein the percentage of sperm cells in the population having abnormal morphology is greater than 25%; b) staining the selected population of sperm cells; c) irradiating the sperm cells in the population; d) detecting fluorescence emitted by the sperm cells in the population in response to the step of irradiating; e) differentiating the sperm cells in the population based on orientation or viability; and f) collecting a subpopulation of oriented or viable sperm cells, wherein oriented or viable X-chromosome and Y-chromosome bearing sperm are collected together.

Yet another embodiment of the invention comprises a method of processing sperm cells comprising a) selecting a population of sperm cells wherein each sperm cell has a cell long axis and wherein greater than 25% of sperm cells in the population have abnormal morphology; b) staining the sperm cells in the population; c) placing the sperm cells in the population in a channel configured to impart orienting forces on the sperm cells that defines a flow axis and through which the sperm cells flow; wherein the cells, when the cell long axis is parallel with said flow axis, have at least a portion that has a flow orthogonal, cell cross-section that is non-circular, wherein the flow orthogonal, cell cross-section has a flow orthogonal, cell cross-section long axis and a flow orthogonal, cell cross-section short axis that is orthogonal to the flow orthogonal, cell cross-section long axis, wherein the channel configured to impart orienting forces on the sperm cells defines an intended, flow orthogonal, cell cross section long axis alignment line and an intended, flow orthogonal, cell cross section short axis alignment line that is orthogonal to the intended, flow orthogonal, cell cross section long axis alignment line; d) orienting cells with the channel such that a cell presented at full orientation during cell irradiation has the cell long axis parallel with the flow axis, the flow orthogonal, cell cross-section long axis aligned with the intended flow orthogonal, cell cross section long axis alignment line; and the flow orthogonal, cell cross-section short axis aligned with the intended, flow orthogonal, cell cross section short axis alignment line; e) irradiating the sperm cells in the population with a source of electromagnetic radiation; f) detecting fluorescence emitted by the sperm cells in the population using a detector, wherein the detector has a detector, flow orthogonal collection angle that defines a flow orthogonal, detector axis and wherein said flow orthogonal, detector axis is substantially coaxial with said intended, flow orthogonal, cell cross section long axis alignment line; and g) creating a gate that excludes a portion of sperm cells in the population, wherein the angle between an excluded cell's flow orthogonal, cell cross-section long axis and the intended, flow orthogonal, cell cross section long axis alignment line is greater than 5°. In a particular embodiment, the angle in step g) is greater than 10°. In an even more particular embodiment, the angle in step g) is greater than 15°. In a yet more specific embodiment, the angle in step g) is greater than 20°, 25°, 30°, 35°, 40°, or 45°.

Another embodiment of the invention comprises a method of processing sperm cells comprising a) selecting a population of sperm cells wherein each sperm cell has a cell long axis and wherein greater than 25% of sperm cells in the population have abnormal morphology; b) staining the sperm cells in the population; c) placing the sperm cells in the population in a channel configured to impart orienting forces on the sperm cells that defines a flow axis and through which the sperm cells flow; wherein the cells, when the cell long axis is parallel with the flow axis, have at least a portion that has a flow orthogonal, cell cross-section that is noncircular, wherein the flow orthogonal, cell cross-section has a flow orthogonal, cell cross-section long axis and a flow orthogonal, cell cross-section short axis that is orthogonal to the flow orthogonal, cell cross-section long axis; d) irradiating the sperm cells in the population with a beam of electromagnetic radiation, the beam having a flow orthogonal optical axis; e) detecting fluorescence emitted by the sperm cells in the population using a detector, wherein the detector has a flow orthogonal collection angle that defines a flow orthogonal, detector axis and wherein the flow orthogonal, detector axis is orthogonal to the flow orthogonal optical axis; and f) creating a gate that excludes a portion of sperm cells in the population, wherein the angle between an excluded cell's flow orthogonal, cell cross-section long axis and the flow orthogonal, detector axis is greater than 5°. In a particular embodiment, the angle in step f) is greater than 10°. In an even more particular embodiment, the angle in step f) is greater than 15°. In a yet more specific embodiment, the angle in step f) is greater than 20°, 25°, 30°, 35°, 40°, or 45°.

DETAILED DESCRIPTION OF THE INVENTION

Figure 1:
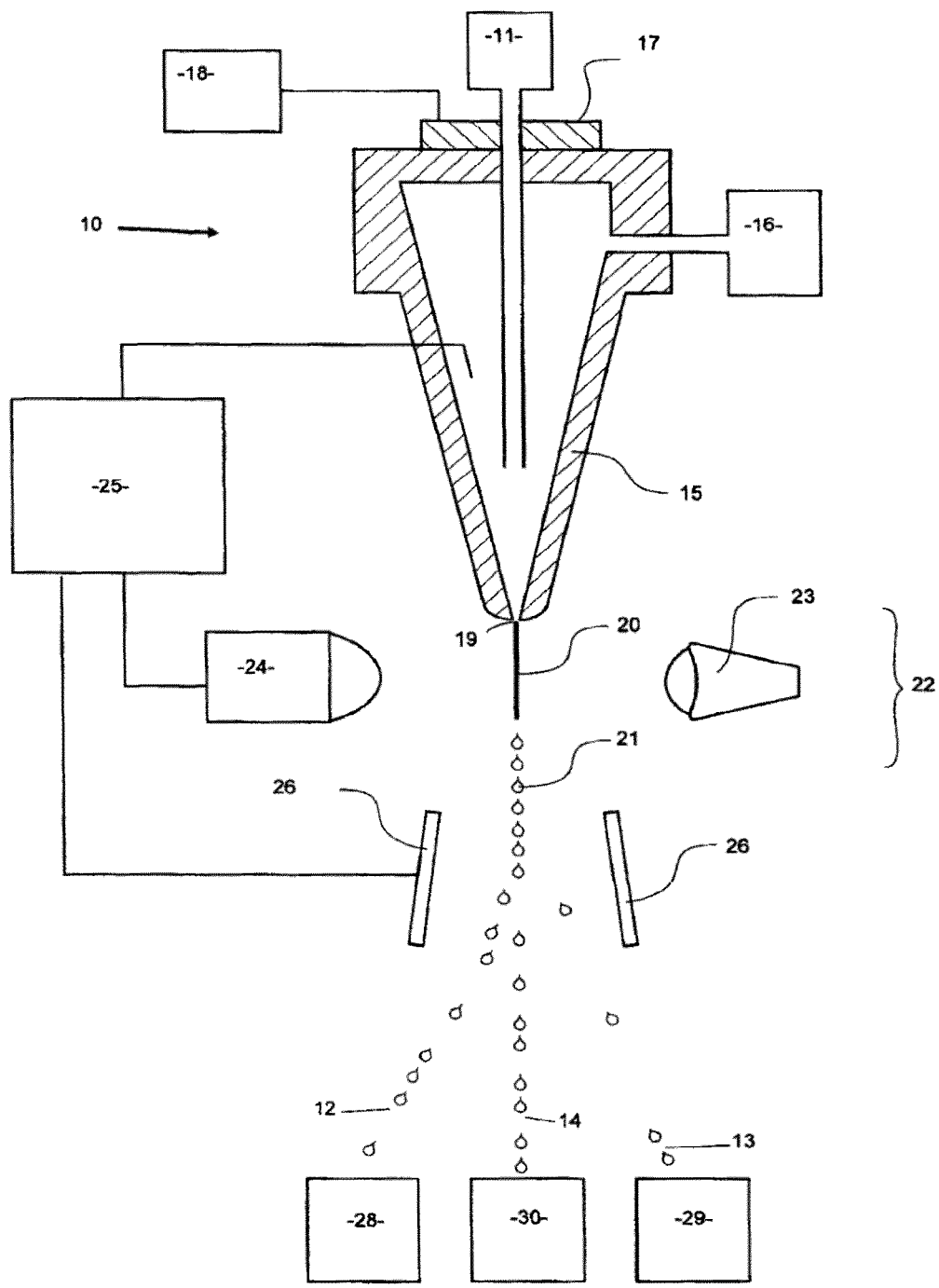
FIG. 1 illustrates, in schematic form, part of a flow cytometer used to analyze and then sort a sperm composition to form one or more subpopulations.

The invention encompasses methods of sorting sperm cell populations to remove those sperm cells with abnormal morphology or nonmotile, or unviable, cells. Sperm cell populations having a higher proportion of cells with abnormal morphology, or a higher proportion of nonmotile or unviable sperm cells, may adversely affect the fertility and conception rates attainable by those sperm cell populations, thereby reducing their efficiency when used in breeding (e.g., in assisted reproductive technology techniques, such as artificial insemination and in vitro fertilization (IVF)).

In the case of high genetic value animals, the impact on genetic dissemination and genetic improvement of the species can be substantial. Thus, by reducing the proportion of these problematic cells within sperm cell populations, the invention yields improved efficiency in their use in breeding.

The term "sperm cell population" includes but is not limited to a raw ejaculate, an ejaculate, including an extended or processed ejaculate, a sperm cell sample, and a semen sample, including an extended or processed semen sample. In some embodiments of the invention, a sperm cell population may comprise sperm cells from one or more non-human mammals.

Obtaining Sperm

The sperm cell populations for use in the invention can be obtained in the form of neat semen (i.e., raw ejaculate), extended sperm cells, frozen-thawed sperm cells or in combinations thereof. The population of sperm cells can be obtained at the same location the methods of the invention are performed, or can be extended in an appropriate sperm cell buffer for transport to a sorting facility. The sperm cell population can be maintained at room temperature, chilled, or even frozen in an appropriate buffer for later use. Obtaining sperm cell populations can be considered acquiring the sperm cells from a mammal, but may also include acquiring sperm cells from storage, such as obtaining a frozen or chilled straw from storage, or even pooling frozen or extended sperm cells.

The population of sperm cells can originate from mammals, such as a non-human mammals listed by Wilson, D. E. and Reeder, D. M., *Mammal Species of the World*, Smithsonian Institution Press, (1993). In a specific embodiment of the invention, the sperm cell population can be obtained from a non-human mammal, and in a more particular embodiment, the non-human mammal is a member of the group consisting of: bovids, suids, equids, ovids eg. sheep, cervids and murids.

At the time of collection, or thawing, or even pooling, sperm may be checked for concentration, pH, motility and/or morphology. Additionally, antibiotics may be added prior to any further processing steps.

Assessing Sperm Cell Motility

Particular embodiments of the invention comprise a step of selecting a sperm cell population having a specific proportion of nonmotile sperm cells, e.g., wherein 65% of the population of sperm cells is nonmotile; wherein 65%, 70%, 75%, 80%, 85%, 90%, or 95%, or more of the population of sperm cells is nonmotile; or wherein 65% or less of the population of sperm cells is nonmotile. For purposes of the invention, a sperm cell that shows any movement, regardless of whether it travels over a distance, is considered motile. For example, a sperm cell with a moving flagellum is considered motile for purposes of the invention.

In a more specific embodiment of the invention, the step of selecting a sperm cell population is based on a determination, or assessment, either by visual inspection or by computer-assisted sperm analysis (CASA), that the sperm cell population has specific proportion, or number, of nonmotile sperm cells, e.g., a determination that 65% of the population of sperm cells is nonmotile; a determination that 65%, 70%, 75%, 80%, 85%, 90%, or 95%, or more of the population of sperm cells is nonmotile; or a determination that 65% or less of the population of sperm cells is nonmotile.

Accordingly, one aspect of the invention comprises assessing the motility of sperm cells within a sperm cell population either by visual inspection or by CASA and determining the proportion or number of nonmotile, or alternatively motile, sperm cells within the cell population. In certain embodiments of the invention, this assessment occurs prior to cell sorting, and in other embodiments this assessment also occurs after cell sorting, and in yet other embodiments this assessment occurs both before and after sorting.

By way of example, one can assess the motility of a sperm cell population as follows (although it is contemplated that any manual or CASA-based procedure or technique established in the art for assessing sperm cell motility in a population of sperm cells can be employed in connection with the invention). Place 500 µl of TALP based media in a 4 ml test tube at 38-38.5° C. Invert the tube containing the sperm cell population to be assessed several times and then remove a 10 µl aliquot from the tube. Add the 10 µl aliquot of sperm cells to the tube containing the 500 µl of TALP based media and mix. Remove 10 µl of fluid from the mixed tube and place the fluid on a previously warmed (38-38.5° C.) and cleaned slide, twice, and cover with one or more slip covers. Visually assess motility on a microscope with a stage warmer temperature set to 38-38.5° C. using the 10× and 20× objective lenses. Determine the percentage of motile sperm after visual inspection using at least 6 fields.

Assessing Sperm Cell Morphology

Particular embodiments of the invention comprise a step of selecting a sperm cell population having a specific proportion of sperm cells with abnormal morphology, e.g., wherein 25% of the sperm cells in the population have abnormal morphology or wherein greater than 5%, 10%, 15%, 20%, 25%, 30%, 35%, 40%, 45%, 50%, 55%, 60%, 65%, 70%, 75%, 80%, 85%, 90%, or 95%, of the sperm cells in the population have abnormal morphology. For purposes of the invention, a sperm cell that displays any of the following is considered to have abnormal morphology: a primary defect, lack of a tail, an acrosome defect, abnormal head shape, abnormal head size, nuclear vacuoles, abnormal nuclear shape, multiple heads, a rolled sperm head, or a nuclear crest.

In a more specific embodiment of the invention, the step of selecting a sperm cell population is based on a determination, or assessment, either by visual inspection or by computer-assisted sperm analysis (CASA), that the sperm cell population has specific proportion, or number, of sperm cells with abnormal morphology, e.g., a determination that 25% of the sperm cells in the population have abnormal morphology; or a determination that greater than 5%, 10%, 15%, 20%, 25%, 30%, 35%, 40%, 45%, 50%, 55%, 60%, 65%, 70%, 75%, 80%, 85%, 90%, or 95%, of the sperm cells in the population have abnormal morphology.

Accordingly, one aspect of the invention comprises assessing the morphology of sperm cells within a sperm cell population either by visual inspection or by CASA and determining the proportion or number of sperm cells within the cell population with abnormal morphology. In certain embodiments of the invention, this assessment occurs prior to cell sorting, and in other embodiments this assessment also occurs after cell sorting, and in yet other embodiments this assessment occurs both before and after sorting. In one embodiment, after sorting, less than 50%, 40%, 30%, 25%, 20%, 15%, 10%, or 5% of sperm cells in the collected subpopulation have abnormal morphology.

A mammalian sperm cell consists of a head and a tail. The tail attaches to the head by the neck (or connecting piece)

and can be divided into the midpiece, principal piece, and end piece. Sperm length in bovids, for example, is approximately 63 μm. The plasma membrane, or plasmalemma, surrounds the entire sperm and is more firmly attached to the caudal margin of the head and along the principal piece. In mammalian species generally, the sperm head is flattened and paddle-shaped; sperm head length in bovids is approximately 8.5 μm, width is 4.5 μm, and thickness is approximately 0.4 μm, for example. The head is formed by the nucleus, acrosome, and postacrosomal sheath. The nucleus, enveloped by the nuclear membrane, comprises most of the head and contains the genetic material in the form of highly condensed DNA. The anterior half of the nucleus is overlaid by the acrosome, which is a specialized vesicle that contains enzymes essential for the sperm to penetrate the oocyte.

A morphologically normal sperm head is paddle-shaped, with a distinct base, smooth contour, and homogeneous appearance. Normal sperm head shape and size are relatively uniform within the exam population. The acrosome covering the proximal half of the head is observed as a thin line on the equatorial segment. The tail is complete, with the midpiece, principal piece and end piece clearly visible and discernable. The midpiece is single, uniformly thick, and with a smooth outline. The tail is straight or only smoothly curved and the end piece is distinguishable and straight.

Generally, sperm abnormalities in the art are classified as primary and secondary defects. Primary defects include: tailless, acrosome defect, abnormal head shape, abnormal head size, nuclear vacuoles, and other head defects such as rolled or multiple heads or nuclear crests. Secondary defects include: proximal cytoplasmic droplet, distal cytoplasmic droplet, bent midpiece, bent tail, coiled tail, and other midpiece defects such as midpiece fractures, midpiece defects involving duplication of the head implantation fossa, accessory tails, double midpieces or defects of the mitochondrial sheath.

Tailless:

Tailless sperm (or detached heads) are commonly observed in low proportions (<5%) in the ejaculate but might be present in very high numbers in cases of pathological sperm accumulation in the excurrent tract. Tailless sperm are considered major defects, regardless of the morphology of the head and attention is required for the identification of highly deformed tailless sperm. Some of the features that help with differentiation include size/shape resembling that of normal sperm, structures that resembles the acrosome and/or the tail insertion fossa, and appearance (texture) similar to other sperm. In cases of sperm accumulation, ejaculates contain large numbers of sperm, virtually no motility, and large percentages of tailless sperm.

Acrosome Defects:

Acrosome defects are characterized by changes to the appearance/shape of the apex of the sperm head, usually involving excess acrosomal matrix and folding of the acrosome over the apex of the sperm head. Membranous vesicles containing granular or membranous inclusions are commonly entrapped in the acrosomal matrix. Acrosome defects can be caused by environmental factors (e.g. increased testicular temperature, stress, toxins), but can also be of genetic origin. Although acrosome defects are sometimes generally referred to as knobbed acrosome, the appearance of this defect varies from indentation and flattening of the head apex, band- or bead-like thickening of the apex, or protrusion from the head ridge. Another presentation of acrosome defects is the ruffled acrosome, which looks 'swollen', vesiculated or wrinkled.

Abnormal Head Shape:

Generally, there is some variation in normal sperm head shape and size among animals, but sperm heads should be fairly consistent within a semen sample from one animal. Normal sperm head shape ranges from somewhat thinner and elongated to shorter and broader forms. Sperm with extreme abnormalities of head form are easily identifiable; however, the identification of more subtle abnormalities may require comparison among several sperm to establish the normal sperm head shape for the sample. Common abnormal sperm head shape abnormalities include tapered heads, which appear narrow in both the acrosomal and postacrosomal regions, and pyriform heads, which have normal-looking, full and round acrosomal region with a narrow postacrosomal region. However, a variety of head shape abnormalities can be observed, in several cases also accompanied by abnormal head size.

Abnormal Head Size:

Likewise, proper classification of head size abnormalities often requires comparison among sperm in the same sample to determine the normal sperm head size. Macrocephalic (i.e., large head) and microcephalic (i.e. small head) sperm are probably consequence of insults to germ cells during mitotic or meiotic division resulting in uneven distribution of nuclear DNA content. It is not uncommon for head size abnormalities to be accompanied by abnormal head shape.

Nuclear Vacuoles:

Nuclear vacuoles are invaginations of the nuclear membrane into the nucleus and appear as dark dots with a bright edge when observed under differential interference contrast (DIC) microscopy. Diadem defect or craters are other names commonly used to refer to nuclear vacuoles. Although multiple vacuoles along the equatorial segment of the head is sometimes believed to be the only presentation of this defect, single or multiple vacuoles can be observed in different locations on the sperm head. Large confluent vacuoles can also be observed, in some cases causing severe deformities of the head shape and size. Since vacuoles are in essence concavities, they appear as a dark dot with a bright edge when observed under DIC microscopy.

Other Head Defects:

Sperm with multiple heads might have normal head structure, but abnormalities of nuclear shape in one or more heads might also be observed. The heads are usually completely separated and the tails are kept together by a common mitochondrial or fibrous sheet. Rolled sperm heads are curved along the long axis to varying degrees with the nucleus showing a "U" shape. Sperm with nuclear crests have a roughed line extending to variable lengths along the long axis of the head and a "Y" shaped nucleus.

Proximal and Distal Cytoplasmic Droplets:

Sperm cytoplasmic droplets are small spherical masses containing vesicles, tubules, and vacuoles. These are normal, remnants of the spermatid residual cytoplasm that remain attached to the neck region after the release of sperm from the seminiferous epithelium into the lumen of the seminiferous tubule (spermiation). During the maturation process along the transit through the body of the epididymis the cytoplasmic droplet moves from this proximal neck position to the distal portion of the midpiece adjacent to the annulus. Upon ejaculation and mixture with the seminal fluid, the distal cytoplasmic droplet is shed. Therefore, both proximal and distal cytoplasmic droplets on ejaculated sperm are abnormal. Droplets are somewhat consistent in size, project to one or both sides of the tail, and usually have a smooth outline. The location, size and contour differentiate cytoplasmic droplets from other midpiece defects.

Bent Midpiece:

Bent midpieces are common defects characterized by a sharp angle bent ranging anywhere from 'elbow-like' with a few degrees up to 1800 angle with retroaxial reflex of the tail. Retained distal cytoplasmic droplets are commonly observed with bent midpieces.

Bent Tail:

Bent tails involve the end piece or the principal piece. The defect is characterized by a tail that looks short with a blunt end when the end piece or the very distal portion of principal piece folds on top of the principal piece; that is why it is important to ensure the entire tail is examined and that the end piece can be discerned. Usually an 'eyelet' is present when the bend involves the mid or proximal portion of the principal piece.

Coiled Tail:

Coiled tails are characterized by multiple bends or coiling involving the midpiece and/or principal piece. Usually all tail segments, and sometimes cytoplasmic material, are enclosed in a common plasmalemma. When the tail coils over the sperm head, it might make it difficult to determine whether the head is normal or not; a judgment call is necessary in these cases to classify the defect as primary or secondary. Bent and coiled tails are commonly observed in cases of hypoosmotic shock.

Other Midpiece Defects:

Midpiece fractures might occur on the sperm neck, as indicated by deviations from the normal angle of attachment. The midpiece-principal piece junction seems to be structurally more prone to fractures, whereas fractures in other points of the midpiece are very uncommon. Three midpiece defects involve duplication of the head implantation fossa: abaxial implantation, accessory tail, and double midpiece. In sperm with abaxial implantation, offset attachment of the tail towards one side of the base of the head is observed. Accessory tails appear as thin appendages to the side of the fully-formed tail. Double midpieces are thickened with a clear separation line between them; the duplication might extend to various degrees along the tail. Two midpiece defects involve the mitochondrial sheath: disrupted mitochondrial sheath and segmental aplasia of the mitochondrial sheath. Disrupted mitochondrial sheaths are characterized by thickened, swollen, and/or roughed midpieces. Segmental aplasia of the mitochondrial sheath is characterized by the presence of abnormally thin segments of the midpiece giving it a roughed appearance.

By way of example, sperm morphology can be visually assessed under 400× magnification using differential interference contrast (DIC), an optics setup that allows the observation of unstained, transparent cells. An example of a DIC optical configuration includes (1) a linear polarizer inserted into the optical pathway between the microscope light port and the condenser, (2) a specialized beam-splitting prism placed in the condenser, (3) a DIC objective with a second beam-splitting prism positioned behind the lens, and (4) a second linear polarizer (analyzer) usually installed in an intermediate tube between the microscope nosepiece and the eyepieces.

By way of example, visual sperm morphology evaluation may be performed using wet-mount, unstained preparations. Using this technique, sperm are first fixed in suspension with formalin, 3 to 5 microliters of the sample are pipetted onto the slide, and the sample is covered with a 22×22 mm coverslip. It is desirable to obtain a thin sample film to ensure that sperm are adequately spread allowing proper examination of individual cells and to maximize the number of sperm in the appropriate focal plane; in contrast, a thick sample film makes evaluation more difficult. To produce a thin sample film, the coverslip can be gently pressed to ensure the sample spreads evenly under the coverslip. A Kimwipe can be used over the coverslip or the slide/coverslip can be flipped over a Kimwipe and pressure applied to the slide rather than the coverslip. This will facilitate removal of excess fluid and improve the quality of the preparation. Although applying some pressure to the coverslip does not result in artefactual abnormalities, care must be taken to avoid sliding the coverslip. Care should be taken by the technician not to examine the same region of the slide more than once. To that end, it is helpful to move the fine focus control in order to better observe all sperm detail during the evaluation.

By way of example, the results of sperm evaluation may be tallied using a differential cell counter and a total of 100 sperm should be classified. For optimal assessment, a sperm head should lay flat on the slide in order to properly evaluate its morphology. Sperm that are not in appropriate focal plane should be ignored and should not be classified, even when obvious tail defects are present, since counts can be biased towards secondary defects. In order to determine if the sperm head is in the appropriate focal plane for evaluation, the fine focus is adjusted and the outline of the sides of the sperm head are evaluated. If the outlines on both sides of the sperm head are not in focus at the same time, then the sperm head is tilted. Sperm heads tilted at a 90° angle are easily recognized because they appear very bright. If the sperm head is in the appropriate focal plane, assessment of sperm morphology can be conducted even when the tail is not in the same plane as the head, since the tail can be properly examined in its entirety by adjusting the focus. Dry areas of the slides should be skipped and sperm in these areas should not be counted during the evaluation. These sperm can be differentiated by a bright halo around the entire cell. Similarly, areas of the slide where sperm are clumped or there is not enough separation to allow the exam of individual cells in their entirety should be ignored. Proper classification is not possible and usually only sperm with obvious defects are counted in these areas, leading to bias. Only areas where individual sperm can be observed in their entirety should be evaluated. Although tailless sperm heads are classified, detached sperm tails should be ignored, regardless of their morphology. In addition, care must be taken not to confuse cytoplasmic material or a bent/coiled midpiece of a detached tail with a microcephalic sperm head.

Adjusting Sperm Cell Concentration and pH

Once obtained, a sperm cell population may be standardized to a predetermined concentration and/or towards a predetermined pH. Each of the predetermined concentration and pH, may be specific to different species, or even to different breeds of animals within a species. In one embodiment, the sperm may be combined with an initial buffer in the form of a high capacity buffer. Examplary buffers may include TRIS citrate, sodium citrate, sodium bicarbonate, HEPES, TRIS, TEST, MOPS, KMT, TALP and combinations thereof. Any buffer having a high capacity for buffering pH may also be employed, and may be used in combination with additional components which promote sperm viability such as egg yolk, and sources of citrates or citric acid. Additionally, antioxidants and antibiotics may be employed in the initial buffer to promote sperm viability.

The initial buffer may be set at a predetermined pH to normalize the pH of all the obtained sperm samples. In one embodiment, the buffer is adjusted to a pH of 7.2. Additionally, semen may become increasingly acidic over time, possibly because of proteins in the seminal fluid, or possibly due to acidic byproducts of dead or dying cells. In either case, the initial buffer introduces enough free proton (e.g. H+) binding sites to maintain pH near the predetermined target. Even in light of the natural tendency for sperm to become more acidic over time, the initial buffer provides a means for stabilizing pH throughout additional processing steps.

As one example, the sperm sample may be diluted in the high capacity buffer in ratios from about 1:1 to about 1:10. The resulting mixture will have a sperm concentration many times below natural sperm concentrations for a particular species. The extended sperm may be centrifuged in order to reconcentrate sperm. Centrifuging the sperm and removing supernatant allows the sperm to be reconcentrated into a predetermined concentration. The predetermined concentration may be selected based on additional sperm processing steps. For example, in the case of sex sorting bovine, sperm may be reconcentrated at between about 2400 million sperm per ml and about 900 million sperm per ml to simulate a natural range of concentrations. Other concentrations, such as between about 1400 million sperm per ml and about 2100 million sperm per ml may or between about 1700 million sperm per ml and about 2100 million sperm per ml may also be achieved for further processing.

Adjusting the sperm concentration and pH may provide a uniform starting point for further processing. For example, a relatively consistent pH and concentration may provide greater predictability in staining sperm, for example with a DNA selective dye. If each sample is adjusted to the same predetermined pH and concentration, fewer trials may be required on each new collection to ensure adequate staining for sex sorting.

Staining Sperm

In one embodiment of the invention, a sperm cell population may be stained in a staining solution. The pH of the staining solution may be maintained at any of a range of pHs; typically this will be in the range of about 5.0 to about 9.0, or in the range of 5.5 to 7.8. The staining solution may be maintained at a slightly acid pH, i.e., from about 5.0 to about 7.0. Typically, the pH is from about 6.0 to about 7.0; from about 6.0 to about 6.5; about 6.2, about 6.5; about 6.6; about 6.7; about 6.8; about 6.9; or about 7.0. Alternatively, the staining solution may be maintained at a slightly basic pH, i.e., from about 7.0 to about 9.0. Typically, the pH is about 7.0 to about 8.0; about 7.0 to about 7.5; about 7.0; about 7.1; about 7.2; about 7.3; about 7.35; about 7.4; or about 7.5.

The staining solution may be formed by using one or more UV or visible light excitable, DNA selective dyes as previously described in U.S. Pat. No. 5,135,759 and WO 02/41906, the contents of each of which are hereby incorporated herein by reference. Exemplary UV light excitable, selective dyes include Hoechst 33342 and Hoechst 33258. Exemplary visible light excitable dyes include SYBR-14 and bisbenzimide-BODIPY® conjugate 6-{[3-((2Z)-2-{[1-(difluoroboryl)-3,5-dimethyl-1H-pyrrol-2yl] methylene}-2H-pyrrol-5-yl)propanoyl]amino}-N-[3-(methyl {3-[({4-[6-(4-methylpiperazin-1-yl)-1H,3'H-2,5'bibenzimidazol-2'-yl] phenoxy}acetyl)amino]propyl}amino)propyl]hexanamide ("BBC") described in WO 02/41906. Each of these dyes may be used alone or in combination; alternatively, other cell permeant UV and visible light excitable dyes may be used, alone or in combination with the aforementioned dyes, provided the dye does not detrimentally affect the viability of the sperm to an unacceptable degree when used in concentrations which enable sorting as described elsewhere.

The staining solution may also comprise a dye quencher, or quenching dye. Staining protocols for sex sorting, or even bulk sorting, sperm typically rely upon the inclusion of F&DC red food dye No. 40 ("red food dye No. 40" or "red 40") and/or yellow food dye No. 4 as quenching dyes. The maximal absorbance wavelengths of these quenching dyes overlaps the maximal emissions wavelengths of fluorescent dyes, including Hoechst 33342 when bound to nuclear or chromosomal DNA. Because red food dye No. 40 and yellow food dye No. 4 differentially permeate membrane-compromised sperm and overlap the emission spectra of the DNA-selective fluorescent dye, FRET (florescence resonance energy transfer) between the light leaving the DNA-stain complex and the dead quenching dye reduces the overall detected intensity of the light emitted from membrane compromised sperm. The quenched, or dampened, fluorescence from these cells provide fewer photons to the detectors resulting in a distinctly lower signal. This distinctly lower signal results in a noticeable separated subpopulation which allows the exclusion ("gating out") of the membrane compromised sperm during the sorting procedure. Since membrane compromised sperm comprises largely non-viable sperm, excluding these cells from the analysis results in an enriched sperm subpopulation with respect to viability in the sorted subpopulation.

The staining solution may be formed using fluorescent polyamides, and more specifically polyamides with a fluorescent label or reporter conjugated thereto. Such labels will fluoresce when bound to nucleic acids. Examples of polyamides with a fluorescent label or reporter attached thereto include, for example, those disclosed in Best et al., Proc. Natl. Acad. Sci. USA, 15 100(21): 12063-12068 (2003); Gygi, et al., Nucleic Acids Res., 30(13): 2790-2799 (2002); U.S. Pat. Nos. 5,998,140; 6,143,901; and 6,090,947, the content of each of which is hereby incorporated herein by reference.

Fluorescent nucleotide sequences may also be used to label the sperm. Such nucleotide sequences fluoresce when hybridized to a nucleic acid containing a target or complementary sequence, but are otherwise nonfluorescent when in a non-hybridized state. Such oligonucleotides are disclosed, for example, in U.S. Patent Application Publication No. 2003/0113765 (hereby incorporated herein by reference).

Antibodies may also be used to label the sperm in a staining solution. In this embodiment, for example, an antibody that targets the cells of interest may be conjugated with a fluorescent moiety (or equivalent reporter molecule). Because the antibody binds to antigens present on only target cells, such cells can be selectively identified based upon their fluorescence (versus the nonfluorescence of an unlabeled cell). Moreover, more than one type of antibody, each antibody having a different fluorescent moiety attached thereto, may be used simultaneously. This allows for differentiation different target cells based upon the differing fluorescence of each.

Luminescent, color-selective nanocrystals may also be used to label sperm in a staining solution. Also referred to as quantum dots, these particles are well known in the art, as demonstrated by U.S. Pat. Nos. 6,322,901 and 6,576,291, each of which is hereby incorporated herein by reference. These nanocrystals have been conjugated to a number of biological materials, including for example, peptides, antibodies, nucleic acids, streptavidin, and polysaccharides, (see, for example, U.S. Pat. Nos. 6,207,392; 6,423,551; 5,990,479, and 6,326,144, each of which is hereby incorporated herein by reference), and have been used to detect biological targets (see, for example, U.S. Pat. Nos. 6,207,392 and 6,247,323, each of which is hereby incorporated herein by reference).

The concentration of the DNA selective or of any other type of dye in the staining solution is a function of a range of variables which include the permeability of the cells to the selected dye, the temperature of the staining solution, the amount of time allowed for staining to occur, the concentration of sperm, and the degree of enrichment desired in the subsequent sorting or enrichment step. In general, the dye concentration is preferably sufficient to achieve the desired degree of staining in a reasonably short period of time without substantially detrimentally affecting sperm viability. For example, the concentration of Hoechst 33342, Hoechst 33258, SYBR-14, or BBC in the staining solution will generally be between about 0.1 µM and about 1.0M; from about 0.1 µM to about 1000 µM; from about 100 µM to about 500 µM; from about 200 µM to about 500 µM; or from about 300 µM to about 450 µM. Accordingly, under one set of staining conditions, the concentration of Hoechst 33342 is about 350 µM. Under another set of staining conditions, the concentration of Hoechst 33342 is about 400 µM. Under still another set of staining condition's the concentration is about 450 µM.

As another example, the concentration of a fluorescent polyamide, such as for example, those described in U.S. Application Publication No. 2001/0002314, will generally be between about 0.1 µM and about 1 mM; about 1 µM to about 1 mM; about 5 µM to about 100 µM; or about 10 µM.

Optionally, the staining solution may also contain additives to enhance sperm quality. Exemplary additives include one or more antioxidants, one or more scavengers of reactive oxygen species, an antibiotic, a growth factor or a composition which regulates oxidation/reduction reactions intracellularly and/or extracellularly.

Once formed, the staining solution may be maintained at any of a range of temperatures; typically, this will be within a range of about 4° C. to about 50° C. For example, the staining solution may be maintained at a relatively low temperature, i.e., a temperature of about 4° C. to about 30° C.; in this embodiment, the temperature is about 20° C. to about 30° C.; from about 25° C. to about 30° C.; or about 28° C. Alternatively, the staining solution may be maintained within an intermediate temperature range, i.e., a temperature of about 30° C. to about 39° C.; in this embodiment, the temperature is at about 34° C. to about 39° C.; about 35° C.; or about 37° C. In addition, the staining solution may be maintained within a relatively high temperature range, i.e., a temperature of about 40° C. to about 50° C.; in this embodiment, the temperature is from about 41° C. to about 49° C.; from about 41° C. to about 45° C.; from about 41° C. to about 43° C.; or about 41° C. Selection of a preferred temperature generally depends upon a range of variables, including for example, the permeability of the cells to the dye(s) being used, the concentration of the dye(s) in the staining solution, the amount of time the cells will be maintained in the staining solution, and the degree of enrichment desired in the sorting or enrichment step.

Uptake of dye by the sperm in the staining solution is allowed to continue for a period of time sufficient to obtain the desired degree of staining. That period is typically a period sufficient for the dye to bind to the DNA of the sperm in the case of DNA-selective dyes. Generally, this will be no more than about 24 hours; no more than about 10 hours; no more than about 2 hours; no more than about 90 minutes; no more than about 60 minutes; or from about 5 minutes to about 60 minutes. In a particular embodiment, the period is about 30 minutes or about 55 minutes.

The length of the staining period and the temperature at which staining occurs are related such that the longer the period of staining, the lower the temperature of staining temperature may be. For example, in one embodiment, the staining may occur at a relatively low temperature and for a period of about 3 hours to about 24 hours. Alternatively, the staining may occur at an intermediate temperature and for a period of about one half hour to about 3 hours. In addition, staining may occur at a relatively high temperature and for a period of about 10 minutes to about 90 minutes. In a particular embodiment, staining may occur at a temperature of about 4° C. for a period of about 24 hours. In another embodiment, staining may occur at a temperature of about 18° C. for a period of about 4 hours. In yet another embodiment, staining may occur at a temperature of about 41° C. for a period of about 30 minutes. In another embodiment, staining may occur at a temperature of about 35° C. for a period of about 55 minutes. Accordingly, in one embodiment, a staining solution is formed comprising low sugar media, sperm and a dye in a concentration from about 100 µM to about 450 µM, and the staining mixture is held for a period of time at a temperature of about 28° C.; about 35° C.; or about 41° C. In another embodiment, the period of time is about 30 minutes; about 55 minutes; or about 3 hours.

As one example, the population of sperm, or a portion of the population of sperm, could be diluted with the first buffer to between $640 \times 10^6$ and $40 \times 10^6$ sperm/ml, to between about $320 \times 10^6$ and $80 \times 10^6$ sperm/ml, or to about $160 \times 10^6$ sperm/ml in the first buffer. The DNA selective fluorescent dye can be added to the sperm suspended in the first buffer in a concentration of between about 10 µM and 200 µM; between about 20 µM and 100 µM, or between about 30 µM and 70 µM. The pH of the first buffer can be between about 6.8 and 7.9; about 7.1 and 7.6; or at about 7.4 in order to help ensure a uniform staining of nuclear DNA. Those of ordinary skill in the art will appreciate the pH can be elevated with the addition of NaOH and dropped with the addition of HCl.

The population of sperm can be incubated between 30-39° C., between about 32-37° C., or at about 34° C. The period of incubation can range between about 20 minutes and about an hour and a half, between about 30 minutes and about 75 minutes, or for about 45 minutes to about 60 minutes. As one example, the population of sperm can be incubated for about 45 minutes at 34° C. Even within a single species, sperm concentration and pH and other factors affecting stainability can vary from animal to animal. Those of ordinary skill in the art can appreciate minor variations for incubating sperm between species and even between breeds or animals of the same breed to achieve uniform staining without over staining a population of sperm.

In one embodiment, a quenching dye and a DNA-selective dye or other dye are applied together in a single treatment. In a further embodiment, the quenching dye is incubated along with the DNA selective dye or other dye at an elevated temperature in the modified TALP which may be at a pH of 7.4. In this embodiment is believed a synergy exists when the sperm standardized at an elevated pH of about 7.2 before staining it at 7.4. In this way, the pH to which the sperm is exposed remains in a constant range with minimal variations. Because both the staining buffer and the initial extender have high buffering capacities, it is believed the natural tendency of sperm to become more acidic over time will be avoided. Additionally, by minimizing the changes in pH seen by the sperm, it is believed the sperm are in a healthier condition to face the various pressures and stresses endured in the sorting process.

Treatment With Magnetic Particles In one embodiment of the invention, magnetic particles are used to treat a sperm cell population prior to flow cytometric or microfluidic sorting. For example, nanoparticles comprising silane coated iron cores and having one or more chargeable surface moieties can preferentially bind to dead or damaged sperm cells through an electrical charge interaction, as demonstrated in U.S. Pat. No. 9,804,153, whose disclosure with respect to the manufacture and use of such particles is hereby incorporated by reference herein. Alternatively, any moiety or antibody that preferentially binds to dead or damaged cells, such as annexin-V, can first be attached to the magnetic particles. Dead or damaged sperm cells bound to the magnetic particles can then be isolated and removed from sperm cell population using a magnet, thereby increasing the proportion of viable sperm cells in the sperm cell population to be sorted.

Sorting to Remove Unviable Sperm Cells or Sperm Cells With Abnormal Morphologies and Sex Sorting One aspect of the invention comprises sorting a population of sperm cells to remove unviable sperm cells, sperm cells with abnormal morphology, or both. Commonly used and well known sperm analysis and sorting methods via flow cytometry are exemplified by and described in U.S. Pat. Nos. 5,135,759, 5,985,216, 6,071,689, 6,149,867, and 6,263,745; International Patent Publications WO 99/33956 and WO 01/37655; and U.S. patent application Ser. No. 10/812,351 (corresponding International Patent Publication WO 2004/088283), the content of each of which is hereby incorporated herein by reference.

One aspect of the invention is based in part on the discovery that sperm cells with abnormal morphology are more likely to fail to orient properly when subjected to orienting forces such as in a flow cytometer. One of the difficulties in accurate quantification of sperm DNA using fluorescence—as required to effectively differentiate sperm cells on the basis of which sex chromosome they are carrying—is the geometry of the sperm head, which is shaped like a paddle in most species. Generally, the intensity of fluorescence is lowest when the flat face of the sperm is oriented toward a fluorescence detector. This flat orientation actually results in the most accurate measure of DNA content within a cell. Thus, if one desires to measure the DNA content of as many cells in a population of cells as possible and as accurately as possible—for example to effectively sex sort sperm cells—it is necessary that as many cells as possible are properly oriented (i.e., the flat face of the sperm cells facing the detector) when fluorescence detection occurs. There are many techniques known in the art used to orient sperm using various forces generated by the flow cytometer and/or microfluidic device, all of which are contemplated for use with the invention. One way in which orientation can be accomplished in a flow cytometer is by using an orienting nozzle such as described in U.S. Pat. No. 6,357,307, which is hereby incorporated by reference in its entirety. In the context of sex sorting applications, two detectors are generally used for detecting fluorescence emitted by sperm cells. One of the detectors is oriented at 00 relative to the optical axis of the laser beam or other source of electromagnetic radiation and is used to measure forward fluorescence, which corresponds to cell DNA content. The second detector is oriented 90° relative to the optical axis of the laser beam or other source of electromagnetic radiation and is used to measure side fluorescence, which corresponds to the orientation of the sperm. Since the fluorescence signal is highest for sperm oriented with their paddle edge toward the side fluorescence detector, only the sperm that emit peak fluorescence to the side fluorescence detector are considered properly oriented, generally. These properly oriented cells will provide the most accurate picture of their DNA content. Conversely, cells that are not properly oriented will provide a less accurate picture of their DNA content, making a determination of which sex chromosome they are carrying more difficult, if not impossible. Thus, when trying to produce a subpopulation of sperm cells that bear a particular sex chromosome, it is often desirable to select only those sperm cells that are properly oriented for the sorting phase or conversely to exclude sperm cells that failed to orient properly from the sorting phase. This can be accomplished by creating a gate.

Flow cytometry or microfluidics based cell sorting and data analysis are based on the principle of gating. Typically, gates are created around populations of cells with common characteristics. In the context of the invention, these characteristics include forward fluorescence and side fluorescence. Once a gate is created, the cells encompassed by the gate, or excluded by the gate, can be subjected to further analysis or processing. Generally, the first step in gating when sorting sperm is distinguishing populations of sperm based on their forward and side fluorescence properties. As noted above, forward and side fluorescence provide an estimate of the DNA content of the cells and their orientation, respectively. Unoriented sperm will generate events having a lower level of side fluorescence, as noted above. Unviable sperm will generate events having a lower level of both forward and side fluorescence due to the presence of a quenching dye within these cells.

In one embodiment of the invention, the events generated by a population of sperm cells are depicted on a bivariate plot, with forward fluorescence and side fluorescence measured along the Y and X axes, respectively. Accordingly, unviable and unoriented sperm cells can be differentiated from viable and oriented sperm cells by their relative positions on such a bivariate plot. By placing a gate around the events generated by a viable and oriented subpopulation, one is able to subsequently remove or separate those gated sperm cells from the unviable and unoriented sperm cells—this is also referred to as bulk sorting. Alternatively, placing a gate around the unviable and unoriented sperm cells would also allow one to remove or separate those sperm cells from the viable and oriented sperm cells. Generally, gates can be applied either to exclude subpopulations from further analysis, processing or examination or to select subpopulations for further analysis, processing or examination. Using analytical software, measurements and statistics can be obtained for various parameters in addition to the number of cells and percentage of cells within a gate. This can include such measurements as median and mean fluorescence intensity. Two-parameter density plots display two measurement parameters, one on the x-axis and one on the y-axis and the events as a density (or dot) plot.

In one embodiment of the invention, a gated subpopulation of viable and oriented sperm cells can be sorted from the ungated sperm cells. In a different embodiment, a gated subpopulation of viable and oriented sperm cells can be subsequently be sex sorted, i.e., further processed to separate X-chromosome bearing sperm from Y-chromosome bearing sperm. This is generally accomplished by placing a subsequent gate around either the X-chromosome bearing sperm cell subpopulation or the Y-chromosome bearing sperm cell subpopulation, which are distinguishable via fluorescence intensity when using a DNA-selective dye due to the presence of a larger of quantity of DNA in X-chromosome bearing sperm cells. Techniques for flow cytometrically sex-sorting sperm are well known in the art, as exemplified by and described in U.S. Pat. No. 9,347,038, whose disclosure with respect to sex sorting sperm cells via flow cytometry is incorporated by reference herein. In a particular embodiment of the invention, a first gate is placed around a subpopulation of viable and oriented sperm cells, and then within that subpopulation of viable and oriented sperm cells, a subsequent gate is placed around either an X-chromosome bearing subpopulation or a Y-chromosome bearing subpopulation. In this embodiment, one or both of the X-chromosome bearing subpopulation and the Y-chromosome bearing subpopulation are collected in separate collection containers. In an even further embodiment, the sex purity of the collected sex chromosome bearing subpopulation is 51-75%, 55-75%, 51-80%, 51-85%, greater than 90%, greater than 92%, or greater than 95%.

In certain embodiments of the invention, sorting of sperm may be accomplished using any process or device known in the art for cell sorting including but not limited to use of a flow cytometer or use of a microfluidic chip, and optionally encompasses techniques for physically separating sperm from each other, as with droplet sorting and fluid switching sorting, and techniques in which sperm bearing the undesired sex chromosome are killed, immobilized, or otherwise rendered infertile, such as by use of laser ablation/photodamage techniques.

A sperm sample to be analyzed via a flow cytometer or microfluidic device is contained in a sample fluid. A sheath fluid is generally used in a flow cytometer or microfluidic device to hydrodynamically focus, entrain or orient sperm in the sample fluid. Generally, the sheath fluid is introduced into a nozzle of a flow cytometer or into a microfluidic device using pressurized gas or by a syringe pump. The pressurized gas is often high-quality compressed air. In certain embodiments of the invention, a stream containing sperm to be analyzed may be comprised of a sample fluid and a sheath fluid, or a sample fluid alone. Optionally, the sample fluid or sheath fluid may also contain an additive, such as, one or more antioxidants, an antibiotic or a growth factor, as discussed above with respect to sperm sample collection. Each of these additives may be added to either fluid in accordance therewith.

FIG. 1 illustrates, in schematic form, part of a flow cytometer used to analyze and then sort a sperm composition to form one or more subpopulations, the flow cytometer being generally referenced as (10). The flow cytometer (10) of FIG. 1 can be programmed by an operator to generate two charged droplet streams, one containing cells within a center sort region charged positively (12), for example, one containing cells within a flanking sort region charged negatively (13) for example, while an uncharged undeflected stream of indeterminate cells (14) simply goes to waste, each stream collected in receptacles (28), (29), and (30), respectively.

Initially, a stream of sperm under pressure, is deposited into the nozzle (15) from the sperm source (11) in a manner such that they are able to be coaxially surrounded by a sheath fluid supplied to the nozzle (15) under pressure from a sheath fluid source (16). An oscillator (17) which may be present can be very precisely controlled via an oscillator control mechanism (18), creating pressure waves within the nozzle (15) which are transmitted to the coaxially surrounded sperm stream as it leaves the nozzle orifice (19). As a result, the exiting coaxially surrounded sperm stream (20) could eventually and regularly form droplets (21).

The charging of the respective droplet streams is made possible by the cell sensing system (22) which includes a laser (23) which illuminates the nozzle exiting stream (20), and the light emission of the fluorescing stream is detected by a sensor (24). The information received by the sensor (24) is fed to a sorter discrimination system (25) which very rapidly makes the decision as to whether to charge a forming droplet and if so which charge to provide the forming drop and then charges the droplet (21) accordingly. The charged or uncharged droplet streams pass between a pair of electrostatically charged plates (26), which cause them to be deflected either one way or the other or not at all depending on their charge into respective collection vessels (28) and (29) to form a subpopulation of sperm cells that fell within the center sort region and a subpopulation of cells that fell within the flanking sort region, respectively. The uncharged non-deflected subpopulation stream containing indeterminate cells go to the waste container (30).

Figure 2:
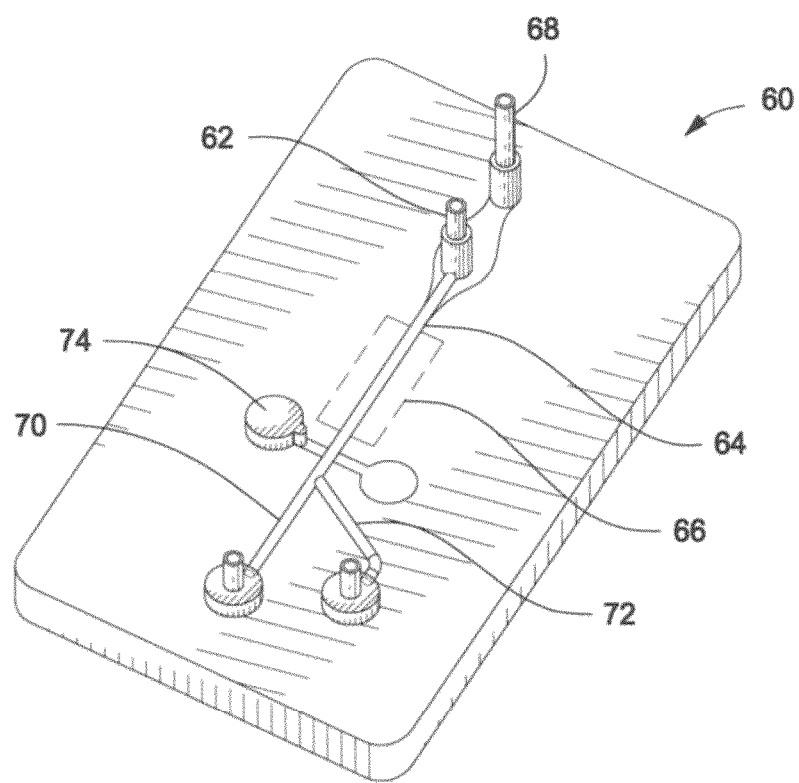
FIG. 2 illustrates a microfluidic device.

Turning now to FIG. 2, an alternative particle sorting instrument is partially illustrated in the form of a microfluidic chip (60). The microfluidic chip (60) may include a sample inlet (62) for introducing sample containing particles or cells into a fluid chamber (64) and through an inspection zone (66). Sample introduced through the sample inlet (62) may be insulated from interior channel walls and/or hydrodynamically focused with a sheath fluid introduced through a sheath inlet (68). Sample may be interrogated at the inspection zone (66) with an electromagnetic radiation source (not shown), such as a laser, arc lamp, or other source of electromagnetic electricity. Resulting emitted or reflected light may be detected by a sensor (not shown) and analyzed with an analyzer (not shown). Each of the sheath pressure, sample pressure, sheath flow rate, and sample flow rate in the microfluidic chip may be manipulated in a manner similar to a jet-in-air flow cytometer, by either automatic adjustments performed by the execution of written instructions in the analyzer or by manual adjustments performed by an operator.

In certain embodiments of the invention, once inspected, particles or cells in the fluid chamber (64) may be mechanically diverted from a first flow path (70) to a second flow path (72) with a separator (74), for altering fluid pressure or diverting fluid flow. The particles or cells may also be permitted to continue flowing along the first flow path (70) for collection. The illustrated separator (74) comprises a membrane which, when depressed, may divert particles into the second flow path (72). Other mechanical or electromechanical switching devices such as transducers and switches may also be used to divert particle flow.

Figure 3:
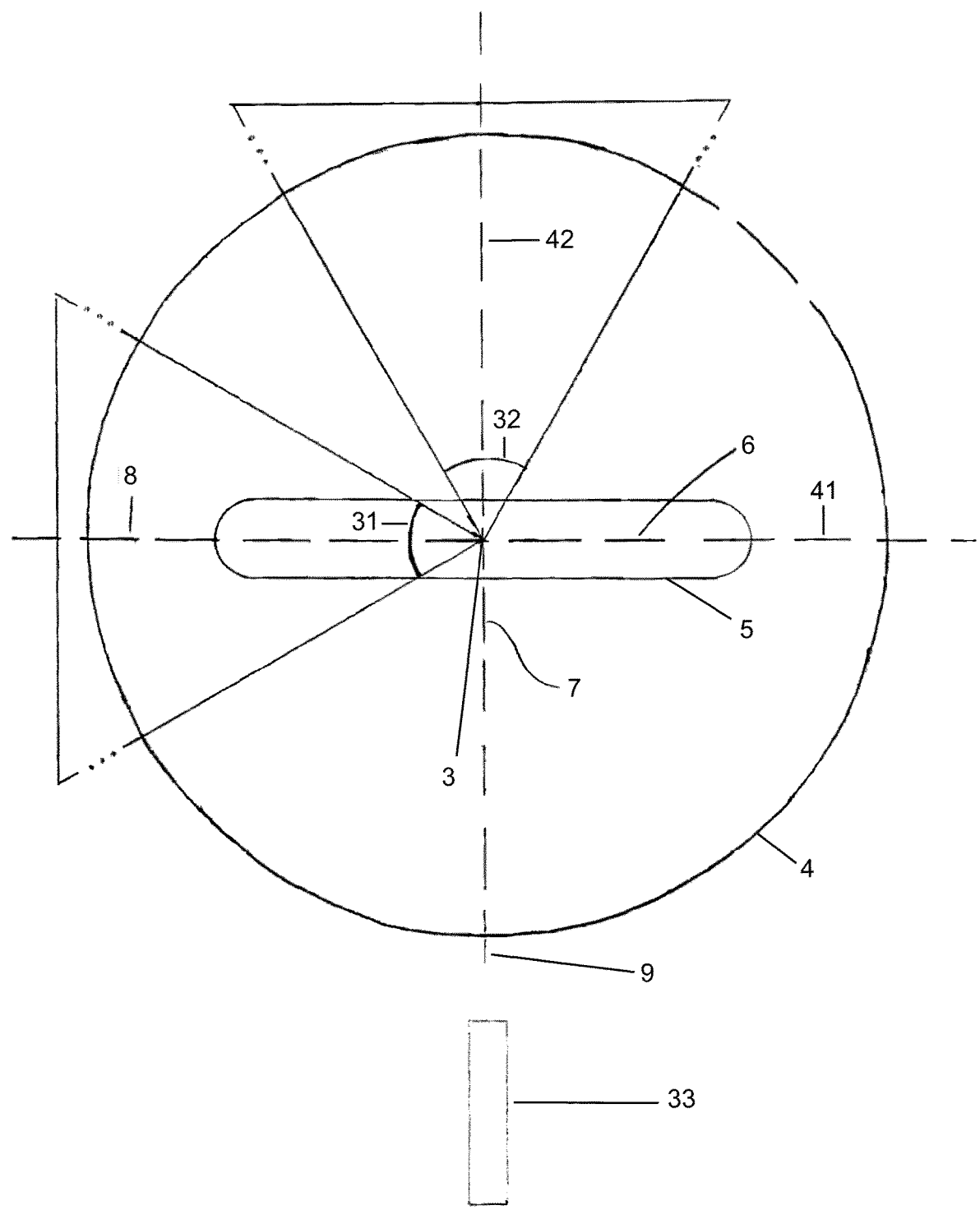
FIG. 3 is a flow orthogonal, cross sectional view of a channel in a cell analysis apparatus.

One aspect of the invention comprises creating a gate that excludes sperm cells that fall outside of a particular parameter for orientation, or conversely, creating a gate that encompasses sperm cells within particular parameter for orientation. Referring to FIG. 3, for purposes of defining a parameter for orientation, a sorting apparatus, whether a flow cytometer or microfluidic chip, comprises a cell source that includes a plurality of cells to be analyzed, each cell defining a cell long axis (3); a channel (4) (e.g., an orienting nozzle tip and/or beveled injection needle that may form an orienting nozzle; or a microfluidic channel) that defines a flow axis and through which the cells flow; wherein the cells, when the cell long axis is parallel with the flow axis, have at least a portion of its head that has a flow orthogonal, cell cross-section (5) (a cross-section of the cell that is orthogonal to the flow when the cell long axis is parallel with the flow axis) that is non-circular. The flow orthogonal, cell cross-section may have a flow orthogonal, cell cross-section long axis (6) and a flow orthogonal, cell cross-section short axis (7) that is, typically, orthogonal to the flow orthogonal, cell cross-section long axis (6). It should be noted that a cell long axis is that cell axis which aligns with a unidirectional flow when the cell is carried by such flow. Further, the term axis, as used in any of the various contexts herein, does not necessarily imply symmetry thereabout; axes, as used herein, may, in instances, be at least conceptually infinite in length.

Referring to FIG. 3, the channel 4 may define an intended, flow orthogonal, cell cross section long axis alignment line (8) and an intended, flow orthogonal, cell cross section short axis alignment line (9) that may be orthogonal to the intended, flow orthogonal, cell cross section long axis alignment line. The term "intended" may indicate that it may be the case that (as is found in most orienting apparatus) fewer than all cells passing through an orienting channel are oriented such that their flow orthogonal, cell cross section long axis aligns with such alignment line (although the intent may be that all cells passing through are so oriented). In this aspect of the inventive technology, the channel may be configured to orient the cells so that each cell presents at full orientation during a cell irradiation, wherein, when the cell is in the full orientation: (a) the cell long axis is parallel with the flow axis, (b) the flow orthogonal, cell cross-section long axis is aligned with the intended flow orthogonal, cell cross section long axis alignment line, and (c) the flow orthogonal, cell cross-section short axis is aligned with the intended, flow orthogonal, cell cross section short axis alignment line.

Referring to FIG. 3, the sorting apparatus may further comprise source of electromagnetic radiation (16) established to effect the cell irradiation by projecting electromagnetic radiation at the cells, and a first detector and a second detector, each established to detect fluorescence emitted as a result of the cell irradiation, wherein the first detector has a first detector, flow orthogonal collection angle (31) that defines a flow orthogonal, first detector axis (41) and the second detector has a second detector, flow orthogonal collection angle (32) that defines a flow orthogonal, second detector axis (42). Detectors may include, inter alia, aperture (which may include a lens), filter(s) and a photomultiplier tube (PMT). It is of note that the detector, flow orthogonal collection angle refers to: (a) the projection of the collection angle onto a flow orthogonal plane when that fluorescent light collected by the detector does not travel in such plane; (b) the collection angle itself where that fluorescent light collected by the detector does travel in such flow orthogonal plane; or (c) a weighted average of collection angles when the associated detector collects electromagnetic radiation expressed over a range of collection angles (as where the detector face that receives electromagnetic radiation is triangular or circular (as but two examples), depending on the detectors' shapes and configuration. The axes defined by collection angles simply bisect such angles; the axes are conceptually infinite in length and, as such, do not terminate at the cell or in the center of any circle (or other figure) defined by the flow. Typically, the flow orthogonal, first detector axis 41 is substantially coaxial with the intended, flow orthogonal, cell cross section long axis alignment line (8), the flow orthogonal, second detector axis (42) is substantially coaxial with the intended, flow orthogonal, cell cross section short axis alignment line (9), and the flow orthogonal, first detector axis (41) and the flow orthogonal, second detector axis (42) may be substantially 90 degrees apart.

EXAMPLE 1

Ejaculates from a bull was assessed for morphological abnormalities. The sperm cell population was stained and then introduced into a flow cytometer for sorting. Three different gates were used to sort the stained sperm cell population (see FIG. 4):

Gate A encompassed sperm cells aligned to the laser at approximately 00 (+/−10-15°), i.e., the flat side of the sperm facing the laser and the forward fluorescence detector—the most oriented cells.

Gate B encompassed sperm cells aligned to the laser at approximately 45°, i.e., the flat side of the sperm rarely facing the laser and out of alignment to both detectors.

Gate C encompassed sperm cells that are not aligned to the laser, with the flat side of the sperm at approximately 90° to the laser and the forward fluorescence detector, i.e., the flat side of the sperm facing the side fluorescence detector, which places the side of the sperm toward the laser beam). This creates a situation in which the laser is only hitting 15-20% of the surface of the sperm head. This decreases signal quality in resolution between X and Y sperm.

Figure 4:
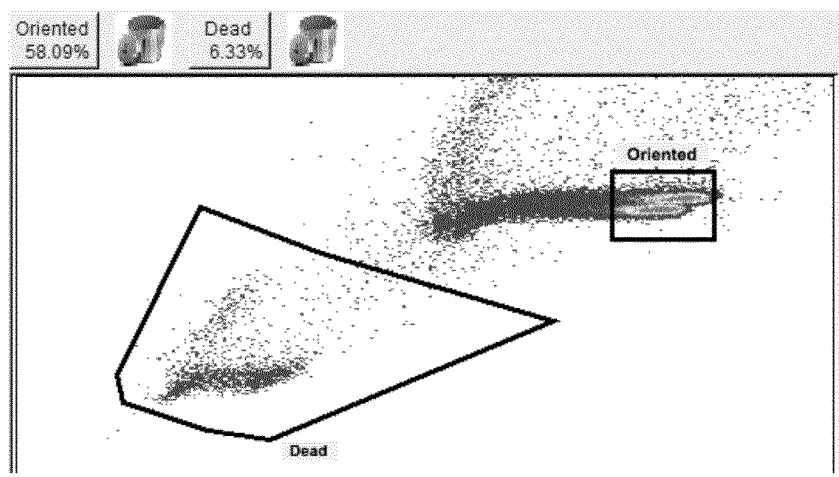
FIG. 4 illustrates three bivariate plots with three different gating regions.
Figure 4:
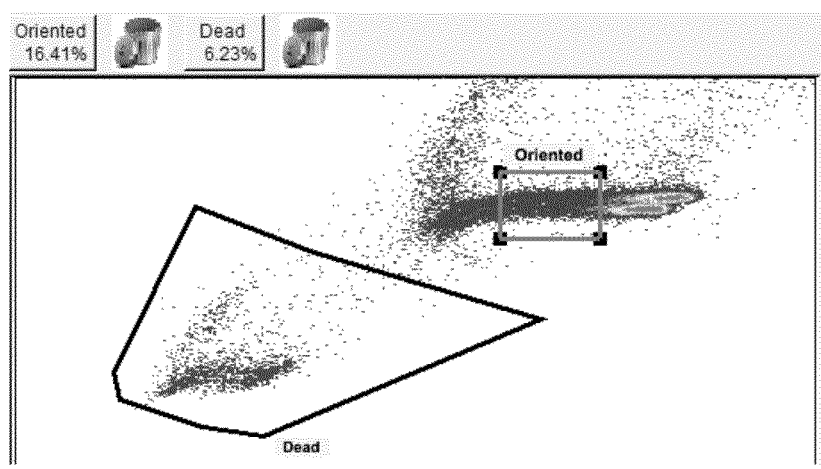
Figure 4:
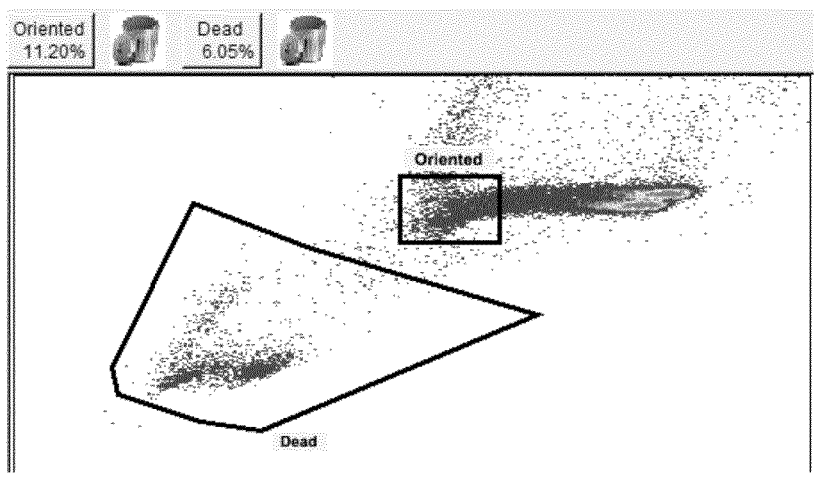

FIG. 4 shows screen captures of three bivariate plots generated by a flow cytometer, with side fluorescence plotted along the X-axis and forward fluorescence plotted along the Y-axis. In FIG. 4, Gate A is shown in the top most plot and is represented by the right most gate on that top plot; Gate B is shown in the middle plot in FIG. 4 and is represented by the right most gate on that middle plot; and Gate C is shown on the bottom most plot in FIG. 4 and is represented by the right most gate on that plot. Relative to Gate A, Gates B and C are shifted to the left. By doing so, progressively less oriented cell populations are being selected. Dead, or unviable, cells (whose fluorescence has been quenched) are encompassed by the left most gate in each plot. Only the cells encompassed by Gates A, B and C were bulk sorted. The gates encompassing the dead cells were created to provide a cell count of the number of dead cells.

Figure 5:
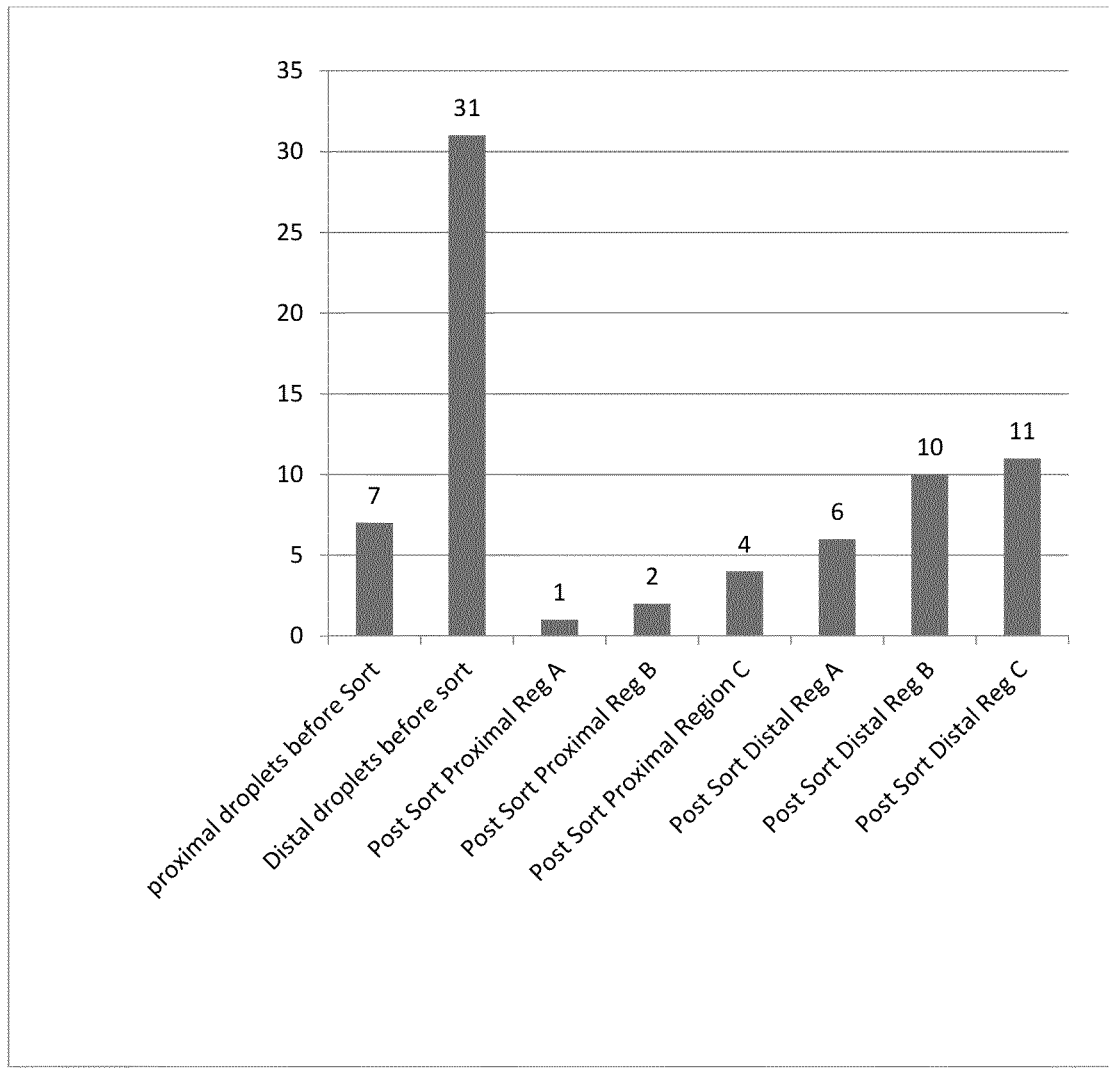
FIG. 5 is a graph showing the reduction in proximal and distal droplets achievable with one embodiment of the invention.
Figure 6:
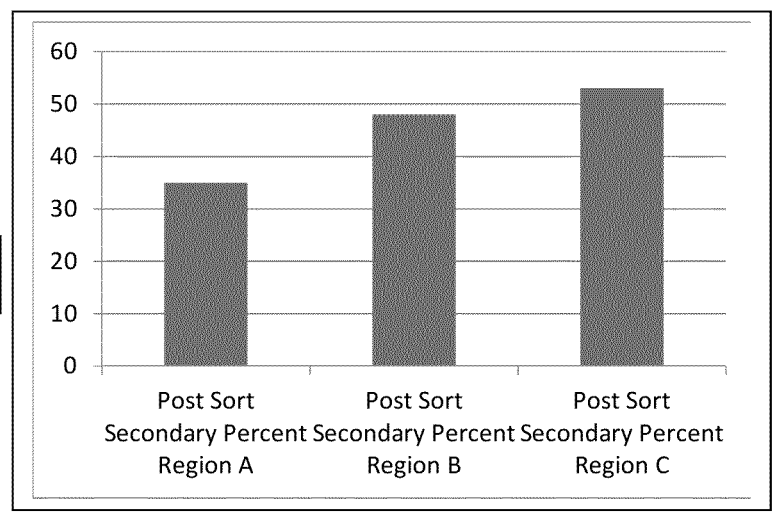
FIG. 6 is a graph showing the reduction in secondary morphological abnormalities achievable with one embodiment of the invention.

Sorting was performed based on these three gates. The results are shown in FIGS. 5 and 6 ("Reg A" or "Region A"=Gate A, "Reg B" or "Region B"=Gate B and "Reg C" or "Region C"=Gate C), which demonstrate that the reduction in secondary morphological abnormalities (e.g., proximal and distal droplets) in the sorted populations improved as cell orientation improved.

EXAMPLE 2

Ejaculates from 6 different Brahman bulls were collected and flow cytometrically sorted.

Treatment Groups:

Conventional (unsorted; dose=25 million sperm cells per ¼ cc straw)

Bulk Sorted (viable oriented cells sorted and collected; dose=8 million sperm cells per ¼ cc straw)

Sex Sorted (viable oriented cells sex sorted and collected; dose=8 million sperm cells per ¼ cc straw)

Magnetic particle treatment pre-sort ("Ultrasep")+bulk sorted (sperm cells treated with magnetic particles to remove dead or damaged sperm cells pre-sort; viable oriented cells sex sorted and collected; dose=8 million sperm cells per ¼ cc straw)

Magnetic particle treatment pre-sort+sex sorted (sperm cells treated with magnetic particles to remove dead or damaged sperm cells pre-sort; viable oriented cells sorted and collected; dose=8 million sperm cells per ¼ cc straw)

1. Collected ejaculates from 6 different Brahman bulls
2. Performed initial check (volume, concentration, motility, morphology of sperm cells). Results are shown in Table 1, below.

| BULL # | ID | Ejaculate | Volume | Conc. | Mot. | Head | Tail |
|---|---|---|---|---|---|---|---|
| B1 | RR1503 | A | 6.8 | 670 | 58 | 27 | 40 |
|  |  | B |  |  |  |  |  |
| B2 | RR1603 | A | 14 | 552 | 70 | 22 | 25 |
|  |  | B |  | 335 | 63 | 23 | 32 |
| B3 | BR1906 | A | 17.5 | 1589 | 70 | 12 | 11 |
|  |  | B |  | 1542 | 66 | 19 | 11 |
| B4 | RR1605 | A | 1.3 | 1358 | 62 | 35 | 12 |
|  |  | B |  | 1170 | 63 | 41 | 17 |
| B5 | RR1478 | A | 13 | 1482 | 56 | 52 | 24 |
|  |  | B |  | 713 | 52 | 40 | 30 |
| B6 | BR1913 | A | 8.4 | 491 | 61 | 31 | 20 |
|  |  | B |  | 385 | 65 | 29 | 20 |

Figure 7:
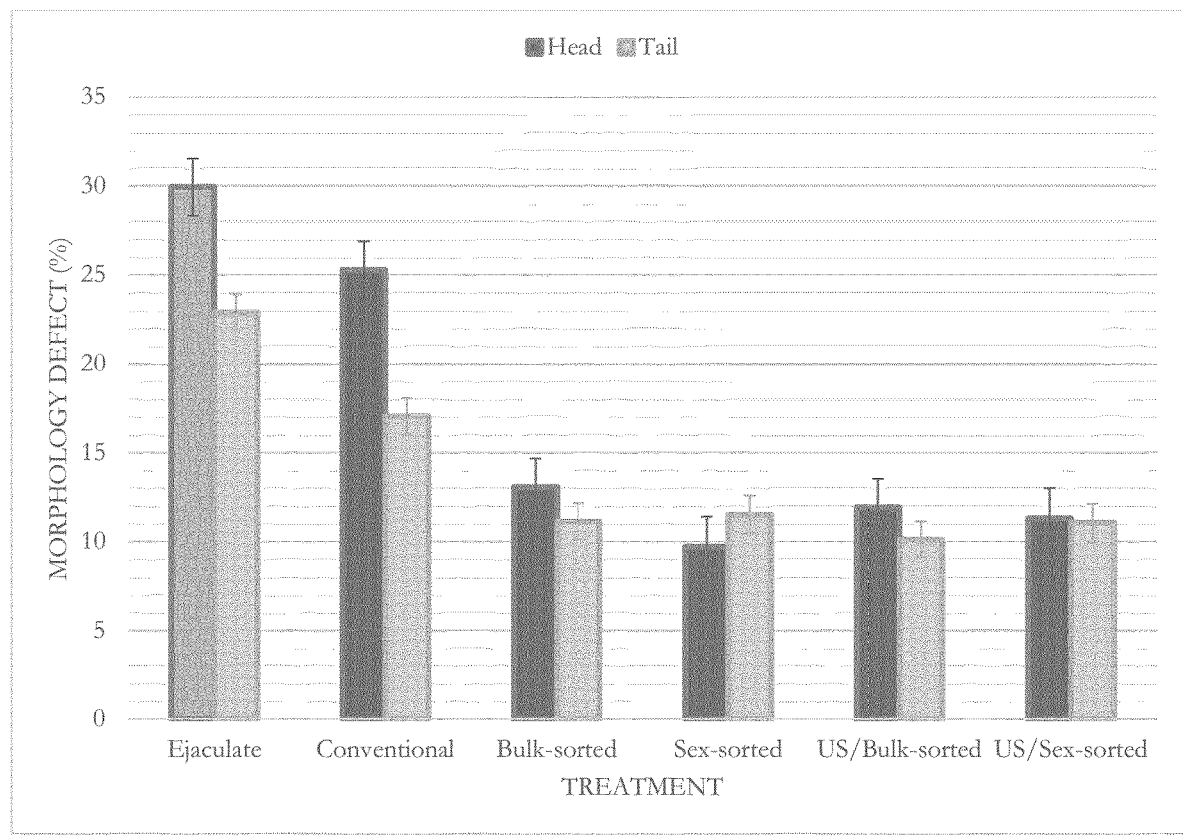
FIG. 7 is a graph showing the reduction in head and tail morphological abnormalities achievable with one embodiment of the invention immediately after thawing.

3. Removed a 1 ml sperm cell sample from each ejaculate and processed following procedures for conventional (i.e., unsorted) semen (25 million cells per ¼ cc straw).
4. Standardized the remaining ejaculate and stained a 40 ml sample per bull with Hoechst 33342.
5. Divided stained sample in two 20 ml samples, aliquots A and B:
   a. Incubated for 60 minutes at 34° C. (aliquot A), and;
   b. Added magnetic particles (100 uL per ml) and incubated both aliquots for 60 minutes at 34° C. (aliquot B).
6. After incubation, added 8% egg yolk TALP-based media and removed magnetic beads from aliquot B.
7. Aligned flow cytometer heads.
8. Established event rate that provides the maximum technical yield.
9. For aliquots A and B, sex-sorted 30 million cells into 7.0 ml of collection media (90% sex purity).
10. For aliquots A and B, bulk-sorted 30 million cells into 7.0 ml of collection media.
11. Once all 4 tubes were sorted per bull, cooled each down for 30 minutes.
12. Centrifuged and added media to adjust final concentration to 8 million cells/straw.
13. Held over-night and froze straws.
14. Thawed one straw per treatment at 38° C. for 45 seconds.
15. Visually assessed head and tail morphological issues immediately after thawing (0 h) on 100 sperm cells under differential interference contrast (DIC) microscopy with a magnification of 400×. Results are shown in Table 2, below and in FIG. 7.

Sperm Morphology

|  | Head | | | Tail | | |
|---|---|---|---|---|---|---|
|  | LSmean | SEM | Group | LSmean | SEM | Group |
| Ejaculate | 29.9 | 1.6 | A | 22.9 | 1.0 | A |
| Conventional | 25.3 | 1.6 | A | 17.0 | 1.0 | B |
| Bulk-sorted | 13.1 | 1.6 | B | 11.1 | 1.0 | C |
| Sex-sorted | 9.7 | 1.7 | B | 11.5 | 1.1 | C |
| US/Bulk-sorted | 11.9 | 1.6 | B | 10.1 | 1.0 | C |
| US/Sex-sorted | 11.3 | 1.7 | B | 11.1 | 1.1 | C |

Figure 8:
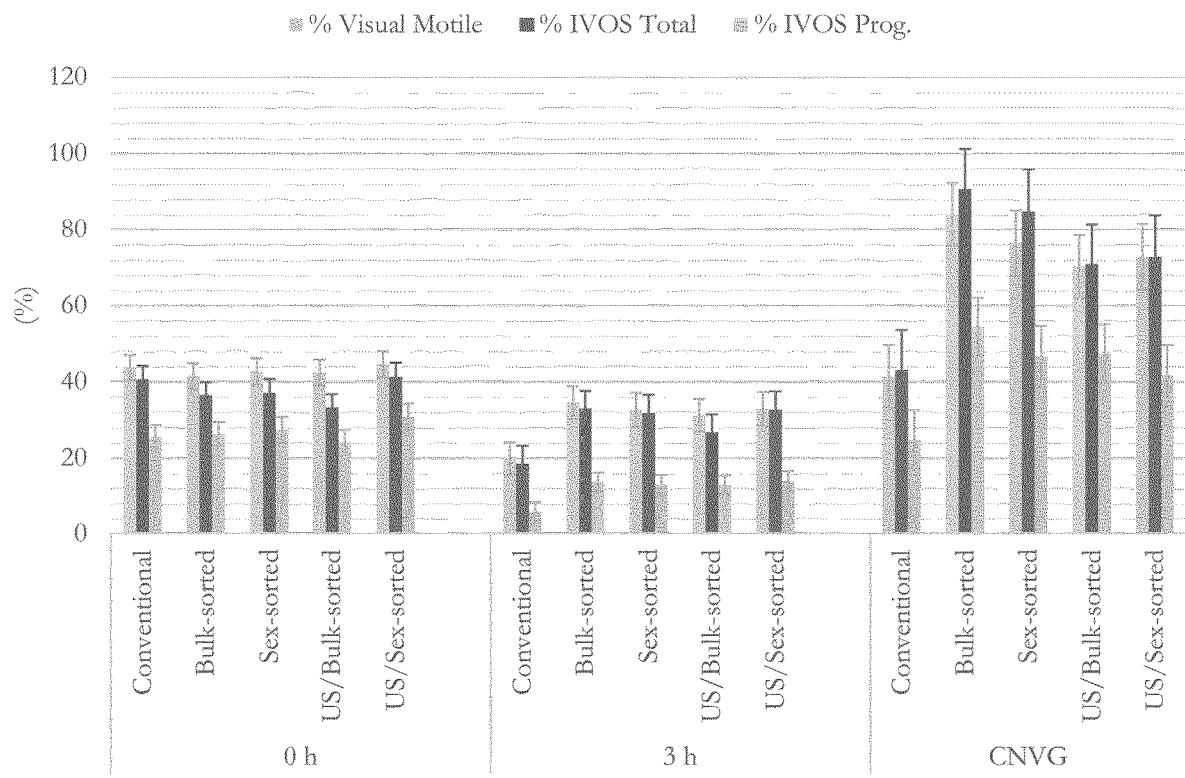
FIG. 8 is a graph showing the increase in motility achievable with one embodiment of the invention immediately after thawing.

16. Estimated post-thaw (0 h) and post-incubation (3 h at 36° C.) percent visual motility at 37° C. on 100 sperm cells under bright field microscopy with a magnification of 200×. Results are shown in Table 3 below.
17. Assessed post-thaw (0 h) and post-incubation (3 h at 36° C.) total motility and progressive motility on a minimum of 500 cells at 37° C. using CASA (in this case IVOS). Results are shown in Table 3 below and in FIG. 8.

Sperm Motility

|  |  | % Visual Motile | | | % IVOS Total | | | % IVOS Prog. | | |
|---|---|---|---|---|---|---|---|---|---|---|
|  |  | LSmean | SEM | Group | LSmean | SEM | Group | LSmean | SEM | Group |
| 0 h | Conventional | 43.6 | 3.4 | A | 40.6 | 3.5 | A | 25.4 | 3.2 | A |
|  | Bulk-sorted | 41.5 | 3.4 | A | 36.4 | 3.5 | A | 26.3 | 3.2 | A |
|  | Sex-sorted | 42.6 | 3.5 | A | 37 | 3.7 | A | 27.3 | 3.4 | A |
|  | US/Bulk-sorted | 42.4 | 3.4 | A | 33.2 | 3.5 | A | 24.1 | 3.2 | A |
|  | US/Sex-sorted | 44.6 | 3.5 | A | 41.3 | 3.7 | A | 30.8 | 3.4 | A |
| 3 h | Conventional | 19.8 | 4.3 | A | 18.5 | 4.7 | A | 5.9 | 2.5 | A |
|  | Bulk-sorted | 34.5 | 4.3 | A | 32.9 | 4.7 | A | 13.7 | 2.5 | A |
|  | Sex-sorted | 32.6 | 4.5 | A | 31.7 | 4.9 | A | 13 | 2.6 | A |
|  | US/Bulk-sorted | 31.1 | 4.3 | A | 26.7 | 4.7 | A | 12.9 | 2.5 | A |
|  | US/Sex-sorted | 32.8 | 4.5 | A | 32.6 | 4.9 | A | 14 | 2.6 | A |
| CNVG (3/0 h) | Conventional | 41.4 | 8.3 | B | 43 | 10.6 | B | 24.8 | 7.7 | A |
|  | Bulk-sorted | 84 | 8.3 | A | 90.6 | 10.6 | A | 54.3 | 7.7 | A |
|  | Sex-sorted | 76.4 | 8.7 | A | 84.7 | 11.1 | AB | 46.6 | 8.1 | A |
|  | US/Bulk-sorted | 70.2 | 8.3 | AB | 70.8 | 10.6 | AB | 47.4 | 7.7 | A |
|  | US/Sex-sorted | 72.8 | 8.7 | AB | 72.7 | 11.1 | AB | 41.6 | 8.1 | A |

Figure 9:
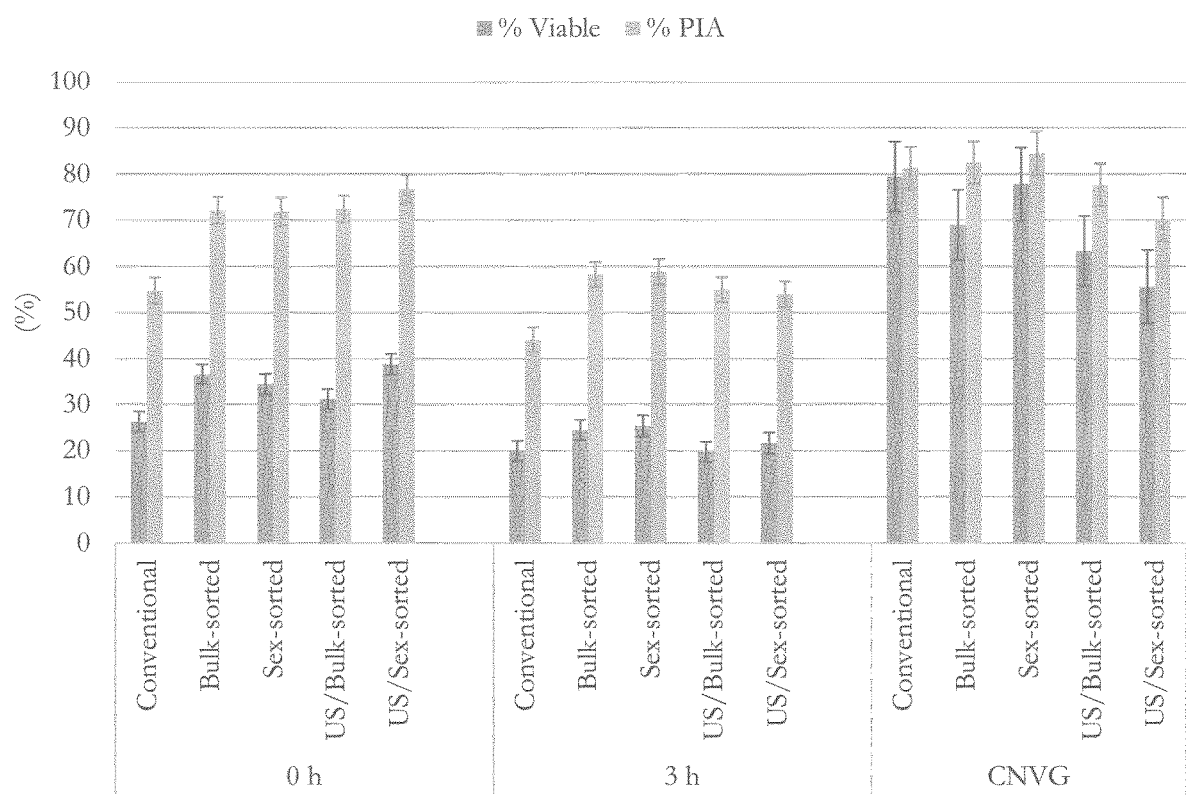
FIG. 9 is a graph showing the increase in viability and percent intact acrosomes achievable with one embodiment of the invention immediately after thawing.

18. Assessed post-thaw (0 h) and post-incubation (3 h at 36° C.) percent viability (VIA) and percent intact acrosomes (PIA) on 10,000 events using an analytical flow cytometer after staining with propidium iodide and FITC-PNA. Results are shown in Table 4, below, and in FIG. 9.

Sperm Via and PIA

|  |  | % VIA | | | % PIA | | |
|---|---|---|---|---|---|---|---|
|  |  | LSmean | SEM | Group | LSmean | SEM | Group |
| 0 h | Conventional | 26.2 | 2.2 | B | 54.7 | 2.9 | B |
|  | Bulk-sorted | 36.6 | 2.2 | A | 72.1 | 2.9 | A |
|  | Sex-sorted | 34.4 | 2.3 | AB | 71.8 | 3.1 | A |
|  | US/Bulk-sorted | 31.1 | 2.2 | AB | 72.4 | 2.9 | A |
|  | US/Sex-sorted | 38.8 | 2.3 | A | 76.7 | 3.1 | A |
| 3 h | Conventional | 19.9 | 2.2 | A | 44.1 | 2.7 | B |
|  | Bulk-sorted | 24.4 | 2.2 | A | 58.2 | 2.7 | A |
|  | Sex-sorted | 25.3 | 2.3 | A | 58.8 | 2.8 | A |
|  | US/Bulk-sorted | 19.7 | 2.2 | A | 55 | 2.7 | A |
|  | US/Sex-sorted | 21.6 | 2.3 | A | 53.9 | 2.8 | AB |

-continued

|  |  | % VIA | | | % PIA | | |
| --- | --- | --- | --- | --- | --- | --- | --- |
|  |  | LSmean | SEM | Group | LSmean | SEM | Group |
| CNVG | Conventional | 79.4 | 7.6 | A | 81.3 | 4.6 | A |
| (3/0 h) | Bulk-sorted | 68.9 | 7.6 | A | 82.4 | 4.6 | A |
|  | Sex-sorted | 77.8 | 7.9 | A | 84.4 | 4.8 | A |
|  | US/Bulk-sorted | 63.3 | 7.6 | A | 77.6 | 4.6 | A |
|  | US/Sex-sorted | 55.6 | 7.9 | A | 70.1 | 4.8 | A |

19. DNA fragmentation (DFI) was assessed post-thaw (0 h) and post-incubation (6, 24, 48 and 72 h, at 36° C.) for both on 300 sperm cells.

Figure 10:
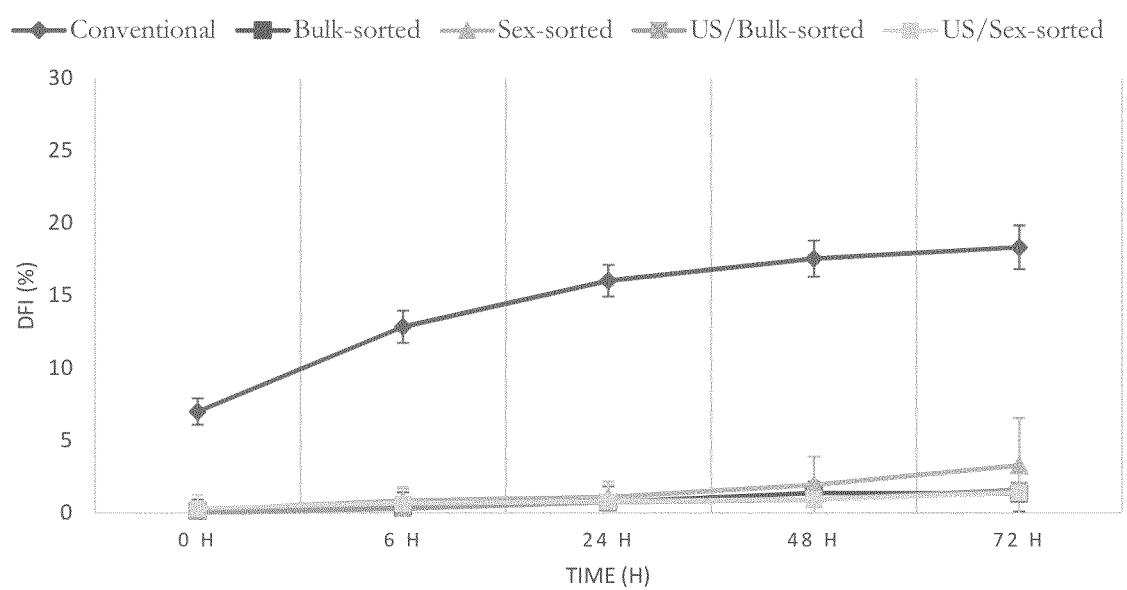
FIG. 10 is a graph showing the reduction in DNA fragmentation achievable with one embodiment of the invention immediately after thawing.

Results are shown in Table 5, below, and in FIG. 10.

Sperm DFI

|  |  | LSmean | SEM | Group |
| --- | --- | --- | --- | --- |
| 0 h | Conventional | 7.0 | 0.9 | A |
|  | Bulk-sorted | 0.2 | 0.9 | B |
|  | Sex-sorted | 0.2 | 1.0 | B |
|  | US/Bulk-sorted | 0.0 | 0.9 | B |
|  | US/Sex-sorted | 0.3 | 1.0 | B |
| 6 h | Conventional | 12.8 | 1.1 | A |
|  | Bulk-sorted | 0.4 | 1.1 | B |
|  | Sex-sorted | 0.8 | 1.2 | B |
|  | US/Bulk-sorted | 0.3 | 1.1 | B |
|  | US/Sex-sorted | 0.6 | 1.2 | B |
| 24 h | Conventional | 16.0 | 1.1 | A |
|  | Bulk-sorted | 0.7 | 1.1 | B |
|  | Sex-sorted | 1.1 | 1.1 | B |
|  | US/Bulk-sorted | 0.7 | 1.1 | B |
|  | US/Sex-sorted | 0.8 | 1.1 | B |
| 48 h | Conventional | 17.5 | 1.3 | A |
|  | Bulk-sorted | 1.4 | 1.3 | B |
|  | Sex-sorted | 1.9 | 1.3 | B |
|  | US/Bulk-sorted | 0.9 | 1.3 | B |
|  | US/Sex-sorted | 0.9 | 1.3 | B |
| 72 h | Conventional | 18.3 | 1.5 | A |
|  | Bulk-sorted | 1.3 | 1.5 | B |
|  | Sex-sorted | 3.3 | 1.6 | B |
|  | US/Bulk-sorted | 1.6 | 1.5 | B |
|  | US/Sex-sorted | 1.4 | 1.6 | B |

EXAMPLE 3

Ejaculates from 5 different Brahman bulls were collected and flow cytometrically sorted.

Treatment Groups:

Conventional (unsorted; dose=40 million sperm cells per ¼ cc straw) Bulk Sorted (viable oriented cells sorted and collected; dose=20 million sperm cells per ¼ cc straw)

Sex Sorted (viable oriented cells sex sorted and collected; dose=20 million sperm cells per ¼ cc straw)

1. Collected ejaculates from 6 different Brahman bulls.
2. Performed initial check (volume, concentration, motility, morphology of sperm cells). Results are shown in Table 6, below.

| BULL # | ID | DATE | MOTILITY | PRI | SEC |
| --- | --- | --- | --- | --- | --- |
| 1 | RR1605 | Sep. 25, 2018 | 75 | 20 | 19 |
| 2 | RR1478 | Sep. 25, 2018 | 60 | 25 | 25 |
| 3 | BR1908 | Sep. 25, 2018 | 75 | 5 | 33 |
| 4 | BR1913 | Sep. 25, 2018 | 75 | 25 | 15 |
| 5 | RR1603 | Sep. 25, 2018 | 70 | 3 | 30 |

Figure 11:
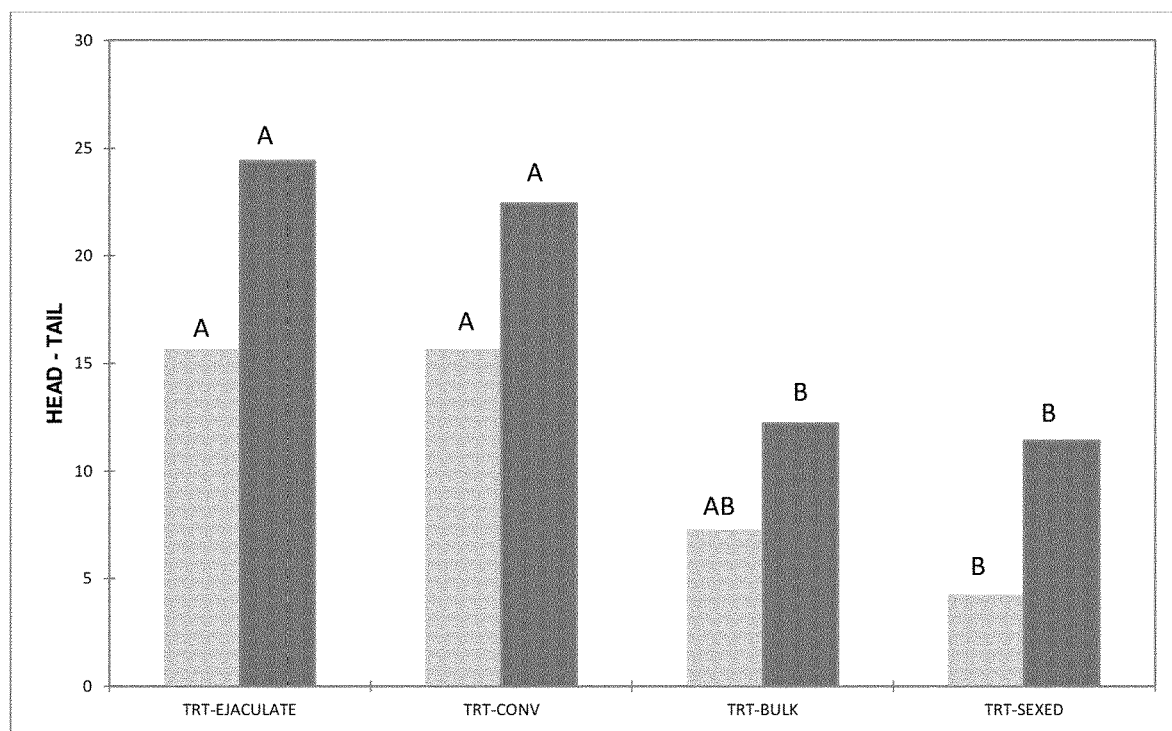
FIG. 11 is a graph showing the reduction in head and tail morphological abnormalities achievable with one embodiment of the invention with unfrozen sperm.

3. Removed a 1 ml sperm cell sample from each ejaculate and processed following procedures for conventional (i.e., unsorted) semen (40 million cells per ¼ cc straw).
4. Standardized the remaining ejaculate and stained a 40 ml sample per bull with Hoechst 33342.
5. Incubated for 60 minutes at 34° C.
6. After incubation, added 8% egg yolk TALP-based media.
7. Aligned flow cytometer heads.
8. Established event rate that provides the maximum technical yield.
9. Sex-sorted 15 million cells into 3.5 ml of collection media (90% sex purity).
10. Bulk-sorted 15 million cells into 3.5 ml of collection media.
11. Extended in media to adjust final concentration to 10 million cells/ml.
12. Split each sample into two aliquots and placed into 1.5 ml Eppendorf microcentrifuge tubes at 36° C. and 18° C.
13. Visually assessed head and tail morphological issues immediately after sorting (0 h) on 100 sperm cells under differential interference contrast (DIC) microscopy with a magnification of 400×. Results are shown in Table 7, below, and in FIG. 11.

Sperm Morphology

|  | Head | | | Tail | | |
| --- | --- | --- | --- | --- | --- | --- |
|  | LSmean | SEM | Group | LSmean | SEM | Group |
| Ejaculate | 15.6 | 2.2 | A | 22.4 | 1.8 | A |
| Conventional | 15.6 | 2.2 | A | 24.4 | 1.8 | A |
| Bulk-Sorted | 7.2 | 2.2 | AB | 12.2 | 1.8 | B |
| Sex-Sorted | 4.2 | 2.2 | B | 11.4 | 1.8 | B |

Figure 12:
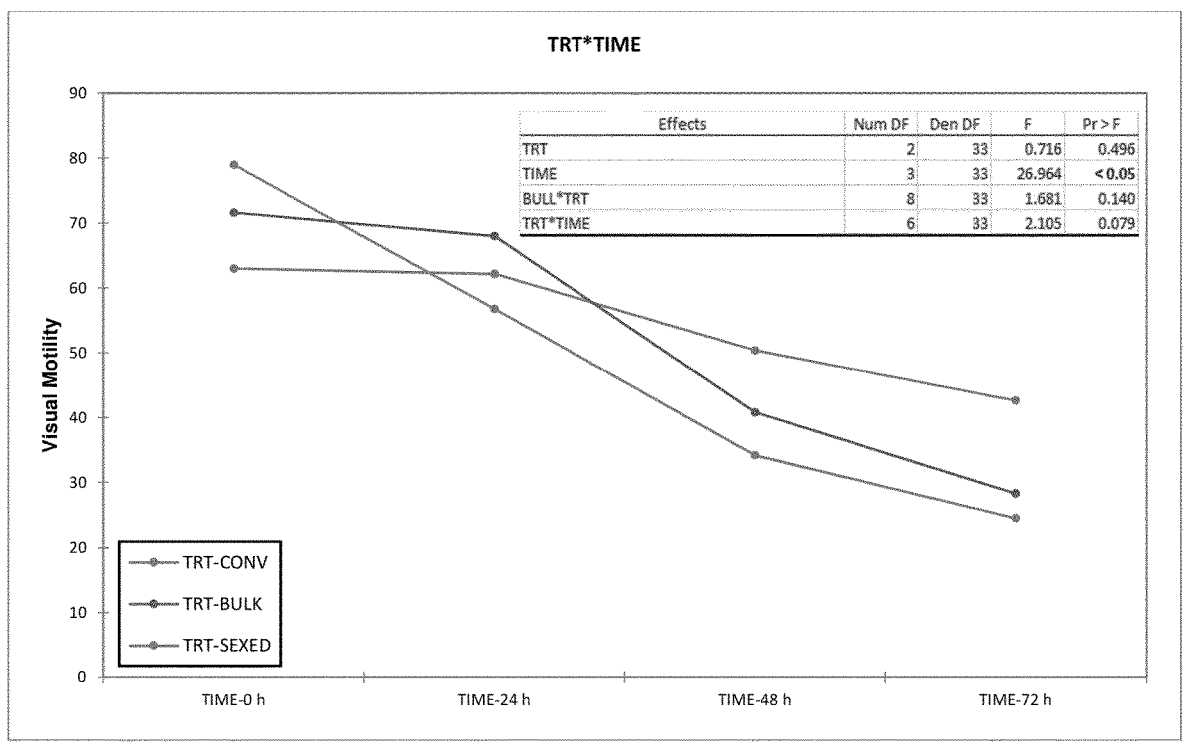
FIG. 12 is a graph showing the increase in visual motility achievable with one embodiment of the invention with unfrozen sperm.
Figure 13:
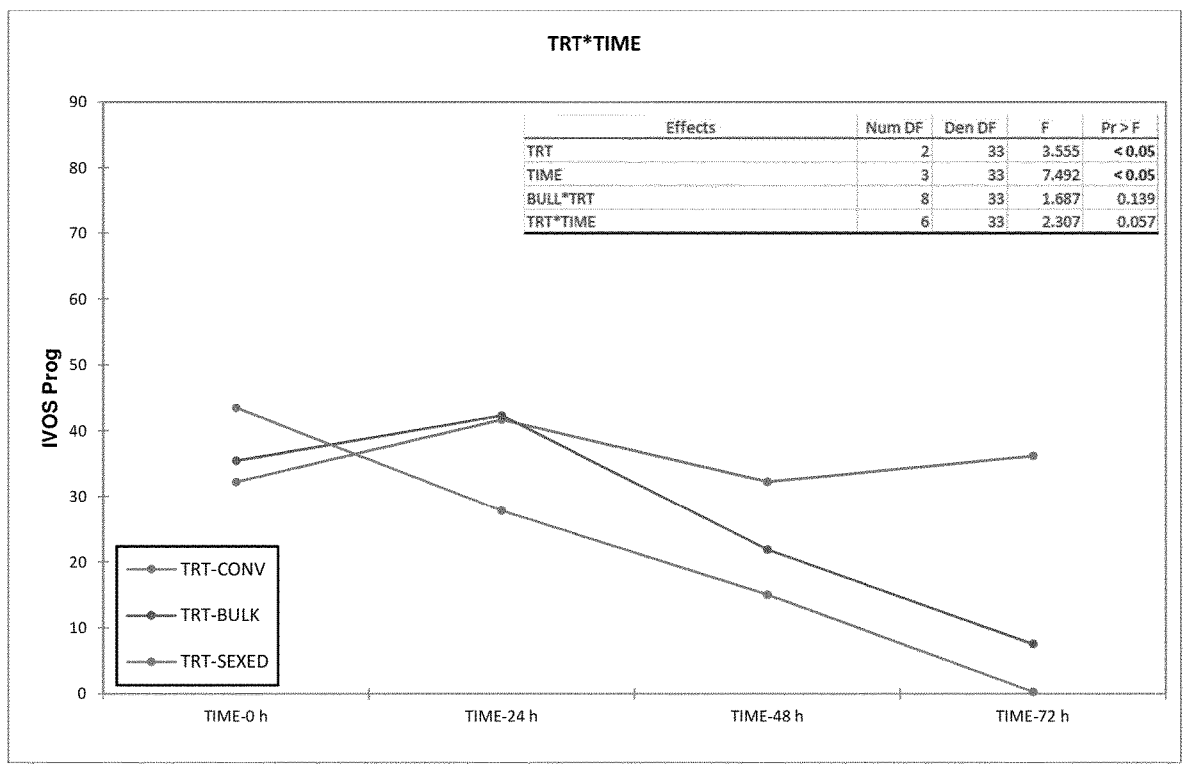
FIG. 13 is a graph showing the increase in progressive motility achievable with one embodiment of the invention with unfrozen sperm.

14. Estimated (0 h) and post-incubation (24, 48 and 72 h at 18° C.) percent visual motility at 37° C. on 100 sperm cells under bright field microscopy with a magnification of 200×. Results are shown in Table 8, below, and in FIG. 12.
15. Assessed (0 h) and post-incubation (24, 48 and 72 h at 18° C.) total motility and progressive motility on a minimum of 500 cells at 37° C. using CASA (in this case IVOS). Results are shown in Table 8, below, and in FIG. 13.

Sperm Quality

|  |  | % Visual Motile | | | % IVOS Total | | | % IVOS Prog. | | |
| --- | --- | --- | --- | --- | --- | --- | --- | --- | --- | --- |
|  |  | LSmean | SEM | Group | LSmean | SEM | Group | LSmean | SEM | Group |
| 0 h | Conventional | 63.0 | 4.6 | ABCD | 63.0 | 4.5 | AB | 32.2 | 3.4 | A |
|  | Bulk-sorted | 71.6 | 4.6 | AB | 75.6 | 4.5 | A | 35.4 | 3.4 | A |
|  | Sex-sorted | 79.0 | 4.6 | A | 75.6 | 4.5 | A | 43.5 | 3.4 | A |
| 24 h | Conventional | 62.2 | 6.6 | ABCD | 61.2 | 8.2 | AB | 41.7 | 8.7 | A |
|  | Bulk-sorted | 68.0 | 6.6 | ABC | 60.4 | 8.2 | AB | 42.3 | 8.7 | A |
|  | Sex-sorted | 56.8 | 6.6 | ABCD | 43.8 | 8.2 | AB | 27.8 | 8.7 | A |

|  | % Visual Motile | | | % IVOS Total | | | % IVOS Prog. | | |
|---|---|---|---|---|---|---|---|---|---|
|  | LSmean | SEM | Group | LSmean | SEM | Group | LSmean | SEM | Group |
| 48 h Conventional | 50.4 | 6.9 | ABCD | 49.5 | 7.8 | AB | 32.2 | 5.8 | A |
| Bulk-sorted | 40.8 | 6.9 | ABCD | 41.3 | 7.8 | AB | 21.9 | 5.8 | A |
| Sex-sorted | 34.2 | 6.9 | BCD | 31.3 | 7.8 | AB | 15.0 | 5.8 | A |
| 72 h Conventional | 42.5 | 5.9 | ABCD | 52.2 | 4.4 | AB | 35.6 | 3.4 | A |
| Bulk-sorted | 24.8 | 5.9 | CD | 16.7 | 4.4 | B | 3.8 | 3.4 | A |
| Sex-sorted | 26.0 | 5.9 | D | 16.6 | 4.4 | B | 1.0 | 3.4 | A |

Figure 14:
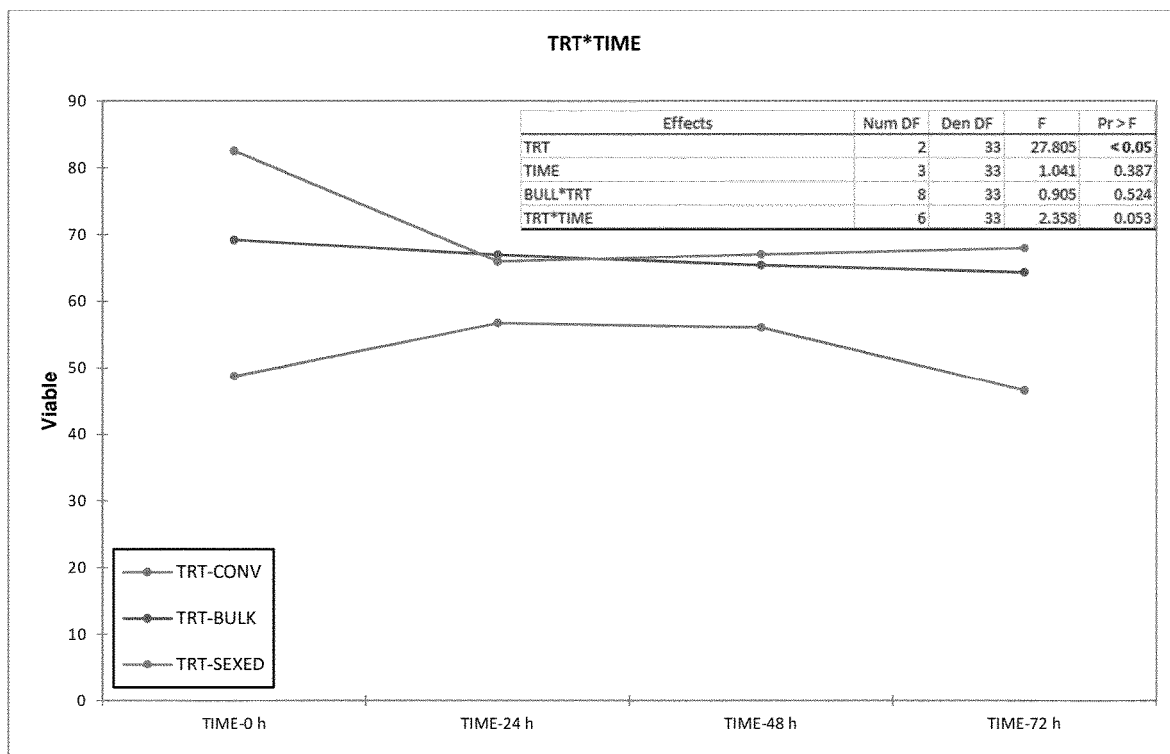
FIG. 14 is a graph showing the increase in viability achievable with one embodiment of the invention with unfrozen sperm.
Figure 15:
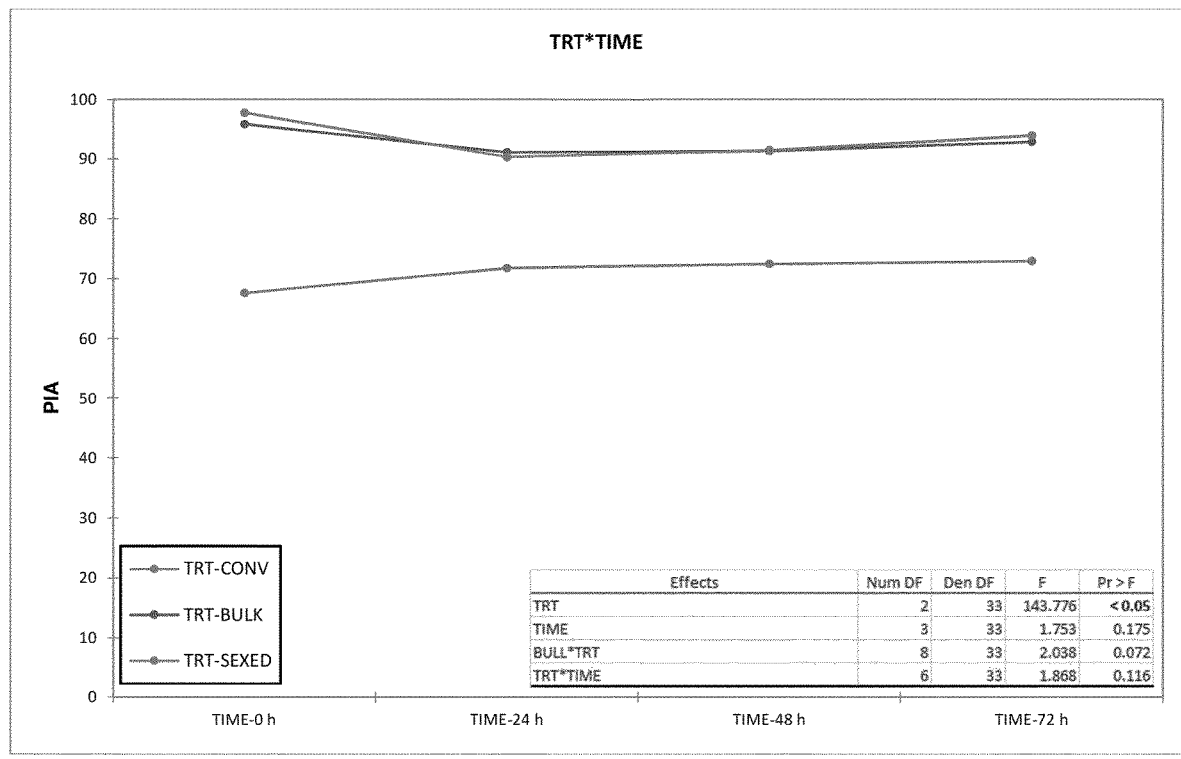
FIG. 15 is a graph showing the increase in percent intact acrosomes achievable with one embodiment of the invention with unfrozen sperm.

16. Assessed (0 h) and post-incubation (24, 48 and 72 h at 18° C.) percent viability (VIA) and percent intact acrosomes (PIA) on 10,000 events using an analytical flow cytometer after staining with propidium iodide and FITC-PNA. Results are shown in Table 9, below, and in FIGS. 14 and 15.

|  | % Viable | | | % PIA | | | % DFI | | |
|---|---|---|---|---|---|---|---|---|---|
|  | LSmean | SEM | Group | LSmean | SEM | Group | LSmean | SEM | Group |
| 0 h Conventional | 48.7 | 4.2 | B | 67.6 | 3.4 | B | 4.3 | 0.6 | B |
| Bulk-sorted | 69.2 | 4.2 | AB | 95.8 | 3.4 | A | 0.3 | 0.6 | C |
| Sex-sorted | 82.5 | 4.2 | A | 97.7 | 3.4 | A | 0.0 | 0.6 | C |
| 24 h Conventional | 91.1 | 2.0 | AB | 71.8 | 2.0 | B | 5.0 | 0.7 | AB |
| Bulk-sorted | 71.8 | 2.0 | AB | 91.1 | 2.0 | A | 0.3 | 0.7 | C |
| Sex-sorted | 90.3 | 2.0 | AB | 90.3 | 2.0 | A | 0.3 | 0.7 | C |
| 48 h Conventional | 56.1 | 3.2 | B | 72.5 | 2.2 | B | 6.5 | 1.0 | AB |
| Bulk-sorted | 65.4 | 3.2 | AB | 91.3 | 2.2 | A | 0.8 | 1.0 | C |
| Sex-sorted | 67.0 | 3.2 | AB | 91.4 | 2.2 | A | 0.5 | 1.0 | C |
| 72 h Conventional | 43.1 | 3.8 | B | 70.2 | 1.7 | B | 7.3 | 1.3 | A |
| Bulk-sorted | 63.7 | 3.8 | AB | 92.6 | 1.7 | A | 0.8 | 1.3 | C |
| Sex-sorted | 66.9 | 3.8 | AB | 93.5 | 1.7 | A | 0.8 | 1.3 | C |

17. DNA fragmentation (DFI) was assessed post-thaw (0 h) and post-incubation (6, 24, 48 and 72 h, at 36° C.) for both on 300 sperm cells.

Figure 16:
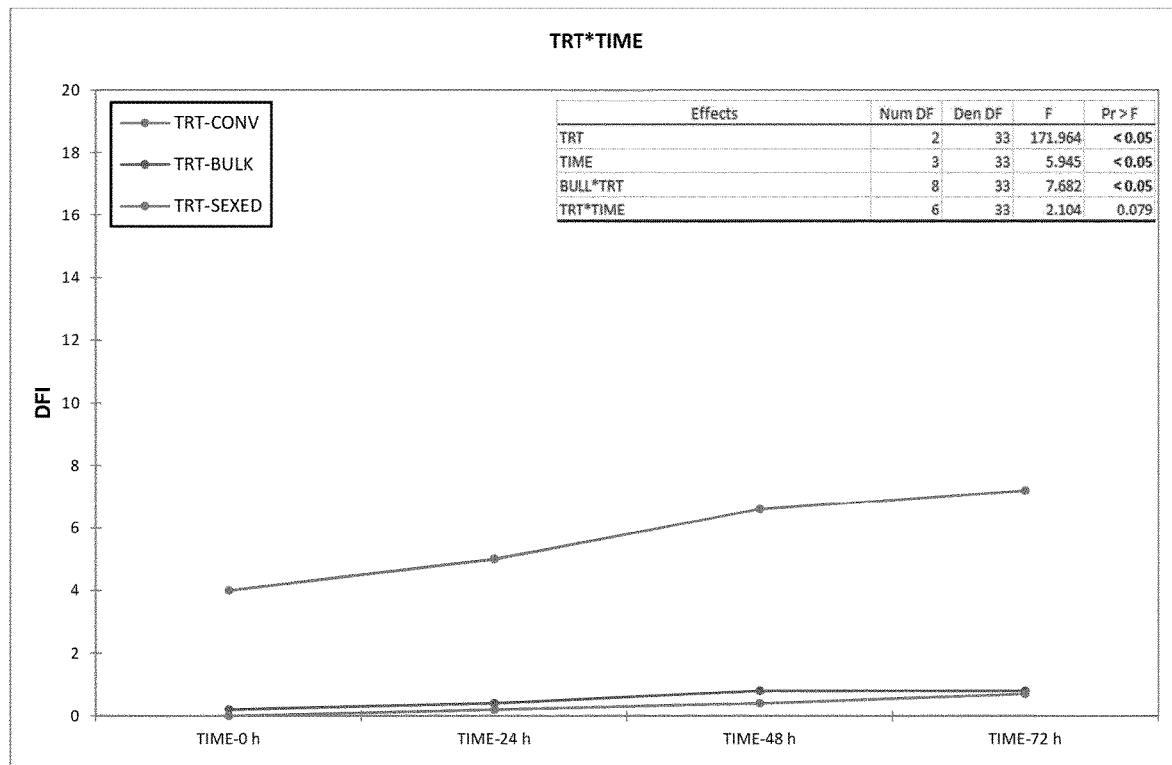
FIG. 16 is a graph showing the reduction in DNA fragmentation achievable with one embodiment of the invention with unfrozen sperm.

Results are shown in Table 9, above, and in FIG. 16.

EXAMPLE 4

Two ejaculates from each of 4 Brahman bulls (n=8) were collected via artificial vagina in Navasota (TX, USA). Only ejaculates with low sperm quality (visual motility of ≤65% and/or total abnormal morphology count ≥25%) were included in the analysis.

Conventional (i.e., unsorted or "non-sorted") sperm was processed using standard industry methods. Ejaculates were first diluted with a Tris-citrate egg yolk medium at 19° C. and then re-diluted in a cold room (4° C.) to a final concentration of 80 million/mL with a Tris-citrate glycerol egg yolk medium. Diluted semen was allowed to equilibrate for a minimum of 90 minutes and then filled and sealed in ¼ cc straws.

Figure 17:
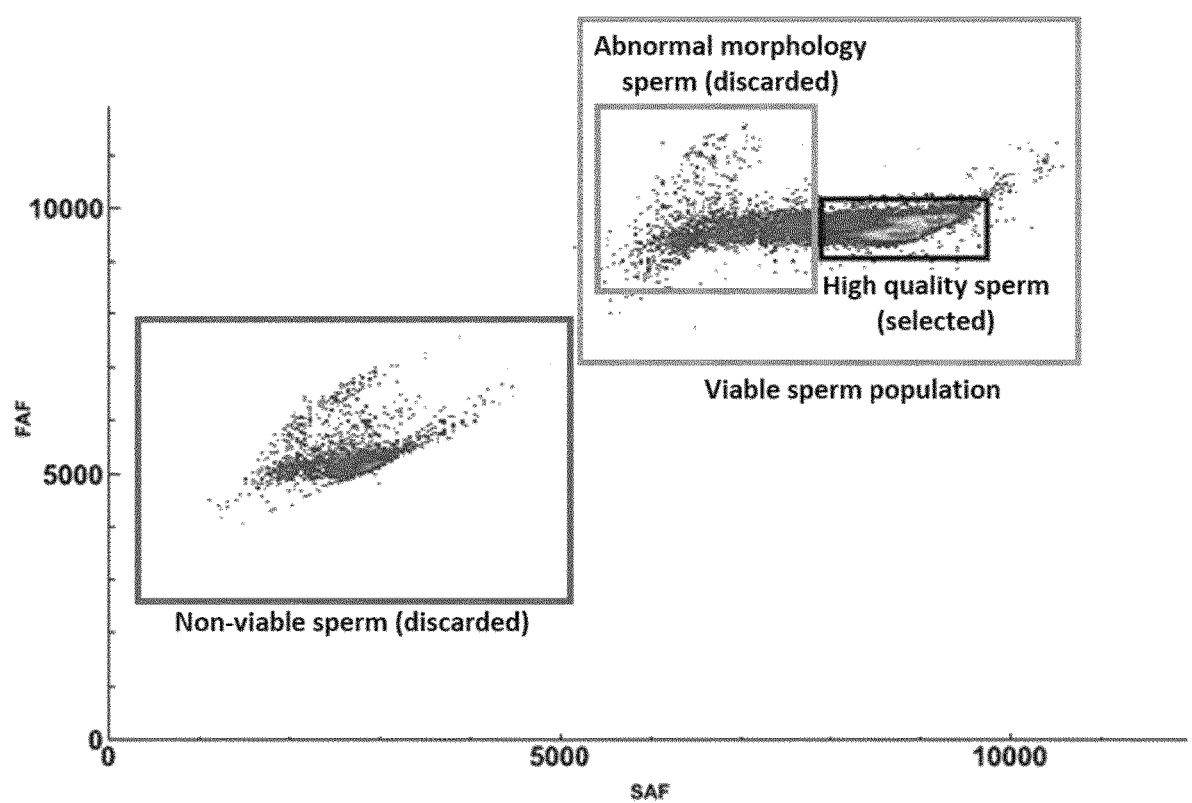
FIG. 17 illustrates a bivariate plot showing separate subpopulations comprising nonviable and viable cells and sperm cells with abnormal morphologies, as well as a gate encompassing oriented and viable cells (gate labeled as "high quality sperm (selected)").

Sorted sperm was processed via flow cytometry by gating on live-oriented sperm region only. Only the front region of the oriented sperm population was selected for sorting (FIG. 17). For the sex-sorted samples, 45% of the X— region was selected to achieve a 90% X chromosome-bearing sperm purity. For the bulk-sorted samples, 100% of the live population was selected to achieve a 50% X chromosome-bearing sperm purity. After sorting, samples were concentrated to 18 million/mL with a Tris-citrate glycerol egg yolk medium, allowed to equilibrate for a minimum of 90 minutes in a cold room, and filled and sealed in ¼ cc straws.

All three treatments were cryopreserved using an automated freezing device, IMV Digitcool (IMV, France) and stored under liquid nitrogen.

Sperm concentration was determined using the SP1-Cassette, Reagent S100, and NucleoCounter SP-100 system (ChemoMetec A/S, Denmark). Visual motility was estimated at 37° C. on 100 sperm cells under bright field microscopy with a Nikon Eclipse 80i microscope (Melville, N.Y., USA) with a magnification of 200×. Visual morphology was estimated at 37° C. on 100 sperm cells under differential interference contrast (DIC) microscopy with a Nikon Eclipse 80i microscope (Melville, N.Y., USA) with a magnification of 400×. Motility on a minimum of 500 cells at 37° C. was classified into total and progressively motile using a computer assisted sperm motility analyzer (CASA-IVOS II system, Hamilton Thorne, Mass., USA). VIA (viability) and PIA (percent intact acrosomes) were assessed on 10,000 events using an analytical flow cytometer (Sexing Technologies, TX, USA) with Summit v5.0 software (Beckman Coulter, FL, USA), after staining Hoechst 33342, Propidium Iodide (Life technologies, IL, USA) and FITC-PNA (Thomas Scientific, NJ, USA). DNA fragmentation (DFI) was assessed on 300 sperm cells using the Bull sperm Halomax® commercial Kit (Halotech DNA, Madrid, Spain).

One conventional, one sex-sorted and one conventional-sorted straw were thawed at 38° C. for 45 seconds. Contents of each straw were placed into pre-labeled 1.5 ml Eppendorf microcentrifuge tubes (Eppendorf North America, NY, USA) at 37° C. Head and tail morphological issues were analyzed immediately after thawing (0 h). Post-thaw (0 h) and post-incubation (3 h at 36° C.) percent visual motility, CASA total and progressive motility, VIA and PIA were assessed. DFI was assessed post-thaw (0 h) and post-incubation (6, 24, 48 and 72 h, at 36° C.) for both procedures.

IVF was performed as a measure of sperm competence using unsorted and sex-sorted straws from four of the ejaculates previously processed. 5-10 oocytes and 5,000 motile sperm/oocyte were placed per IVF drop for the analysis. A total of three straws and 200 oocytes per treatment group (ejaculate×treatment) were included in the comparison for development to 8 cell stage (% cleavage rate) and to day 7 blastocyst stage (% embryo) production.

Statistical analyses were conducted using XLSTAT, version 2018.5 (Addinsoft, NY, USA). For all measures, least-squares means (LSMean) with the standard error of the mean (SEM) are presented. Sperm quality data were analyzed by a mixed model with the fixed effect of treatment and time, and random effect of ejaculate and bull. The mixed model was used in conjunction with a Tukey contrast to analyze the treatment effects across the time points of incubation. The treatment by time interaction was also analyzed to determine collinearity. Sperm morphology and IVF data were analyzed by a mixed model with the fixed effect of treatment and random effect of bull. Differences were considered significant at $P<0.05$.

Figure 18:
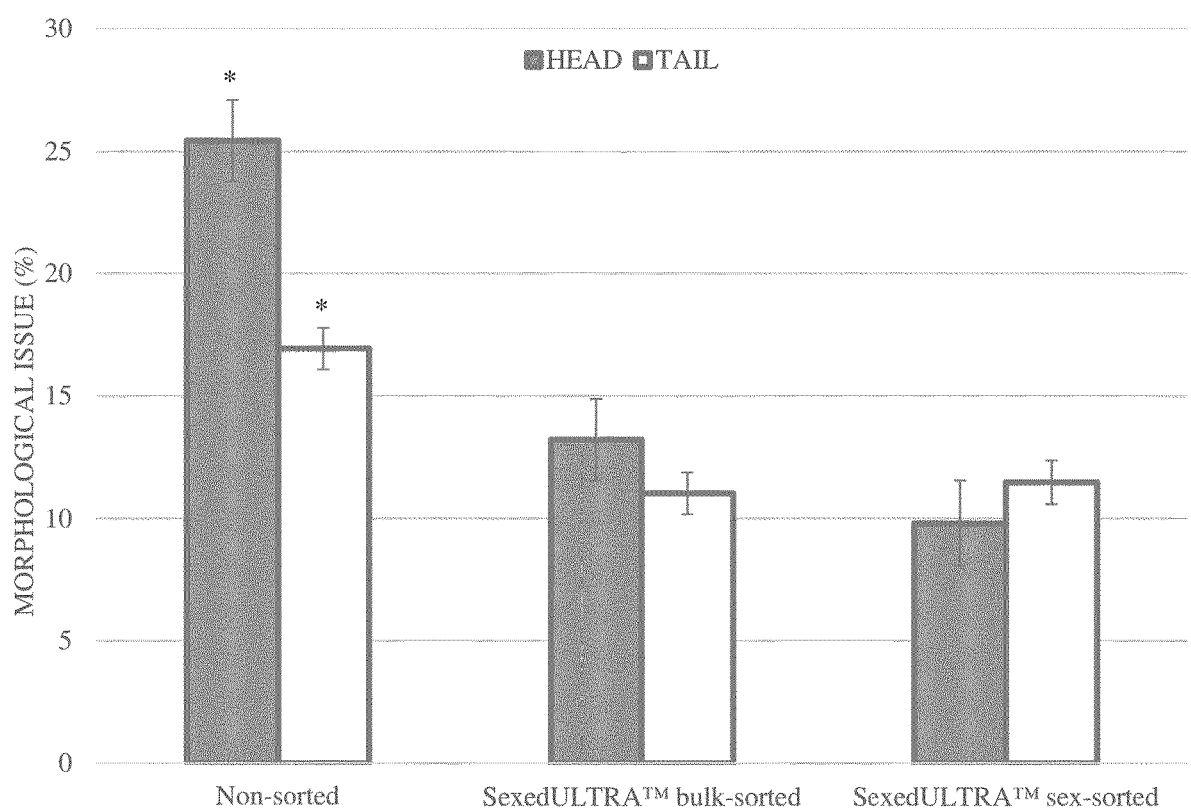
FIG. 18 is a graph showing the reduction in head and tail morphological abnormalities achievable with one embodiment of the invention, including for bulk sorted and sex sorted sperm cell populations.

Results show that frozen-thawed sex-sorted and bulk-sorted sperm head (9.80±1.74 and 13.20±1.66) and tail (11.47±0.89 and 11.02±0.85) abnormal morphologies were significantly lower ($P<0.05$) when compared to unsorted sperm head (25.43±1.66) and tail (16.93±0.85) abnormal morphologies (See FIG. 18).

Figure 19:
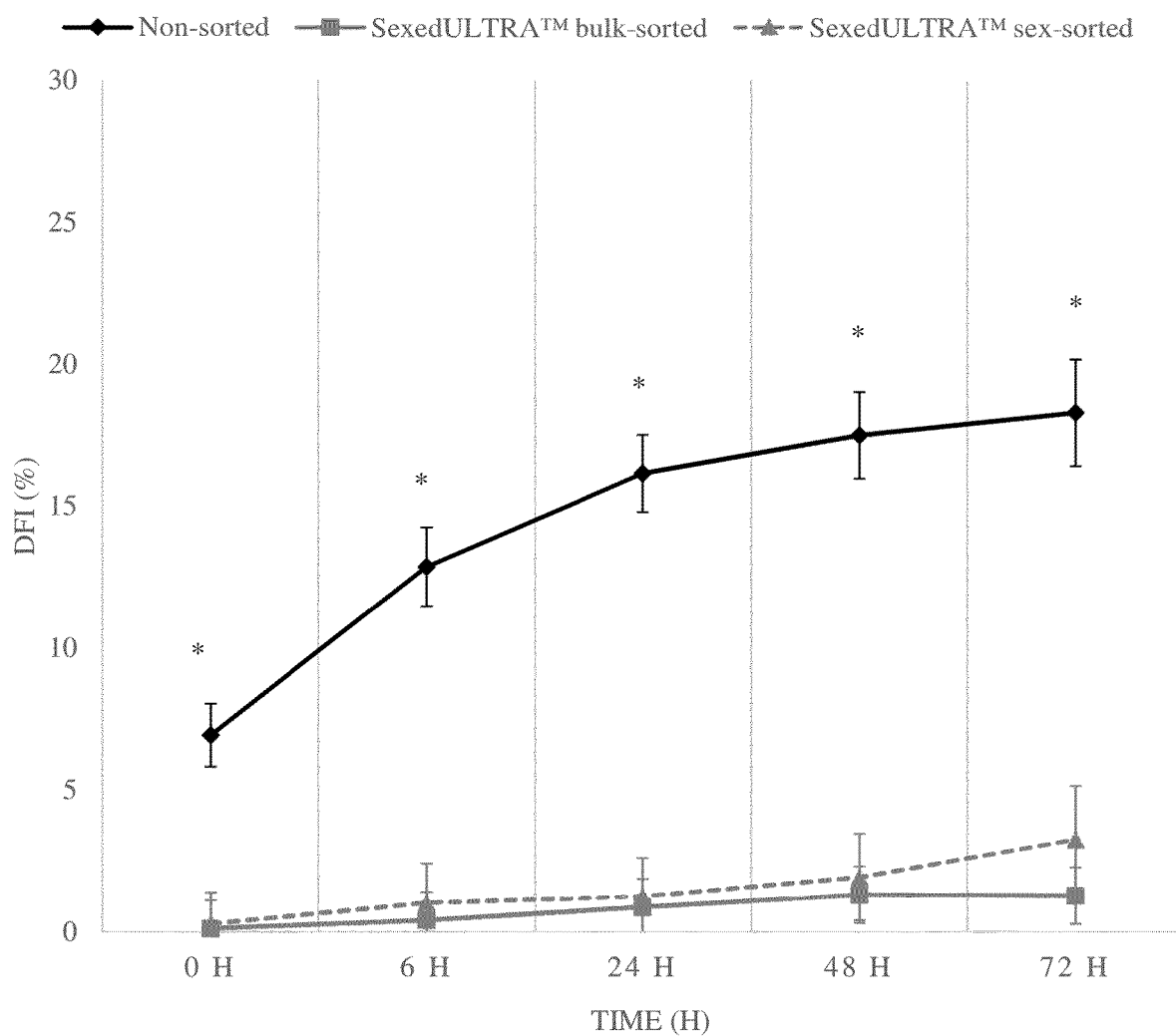
FIG. 19 is a graph showing the reduction in DNA fragmentation achievable with one embodiment of the invention, including for bulk sorted and sex sorted sperm cell populations.
Figure 20:
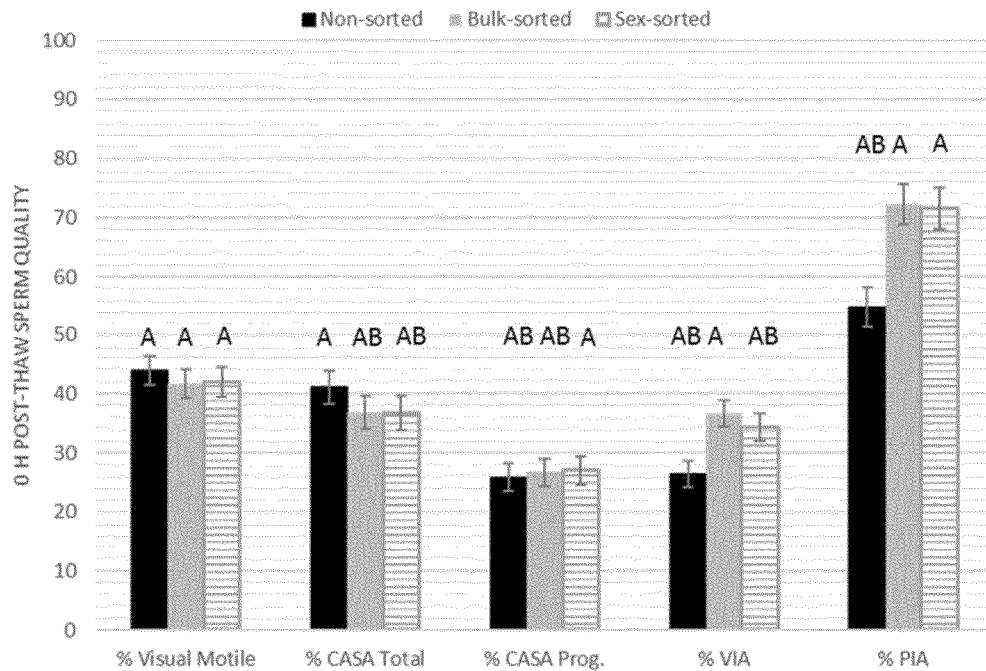
FIG. 20 is a graph showing the increase in percent intact acrosomes achievable with one embodiment of the invention, including for bulk sorted and sex sorted sperm cell populations at 0 hr. post-thaw.
Figure 21:
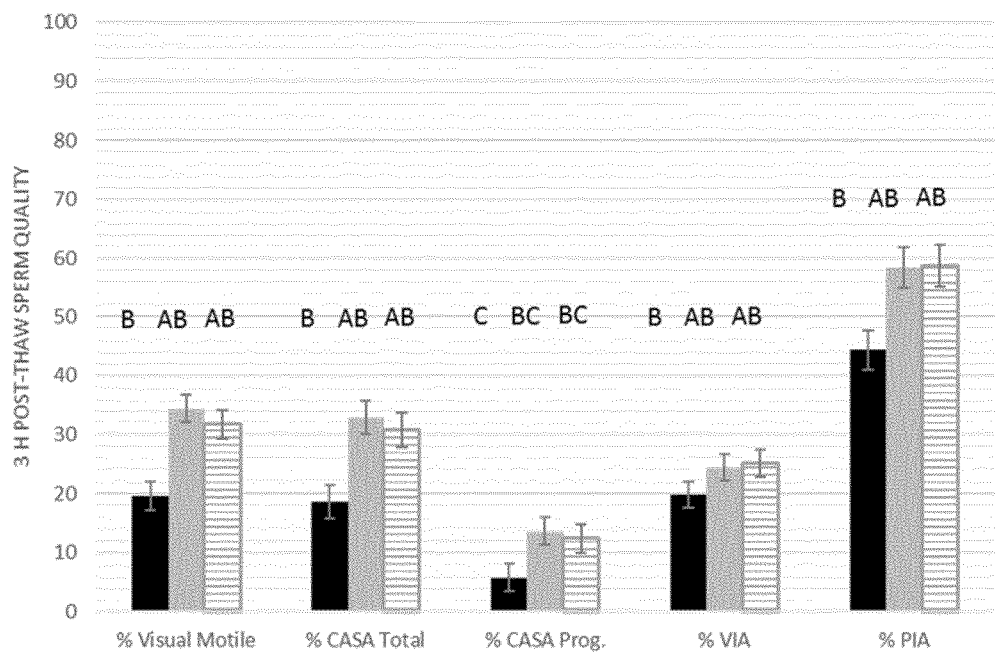
FIG. 21 is a graph showing the increase in visual motility, total motility, progressive motility, viability and percent intact acrosomes achievable with one embodiment of the invention, including for bulk sorted and sex sorted sperm cell populations at 3 hr. post-thaw.

Significant differences ($P<0.05$) were also found in percent DFI between sex- and bulk-sorted, and unsorted sperm immediately after thawing (0.28±1.17 and 0.11±1.11 vs 6.93±1.11), and after 6 h (1.02±1.46 and 0.40±1.39 vs 12.86±1.39), 24 h (1.25±1.42 and 0.88±1.36 vs 16.15±1.36), 48 h (1.93±1.60 and 1.31±1.53 vs 17.49±1.53) and 72 h (3.26±1.97 and 1.28±1.88 vs 18.28±1.88) of incubation at 36° C. (See FIG. 19). Other than PIA, all other parameters at 0 h (see FIG. 20) were not significantly different for the sorted compared to unsorted sperm samples due to the large differences in post-thaw quality between bulls. However, numerical differences were clear between sex- and bulk-sorted compared to unsorted sperm at 3 h post-incubation for percent visual motility, total and progressively CASA motility, VIA and PIA (see FIG. 21).

In all cases, a significant bull and ejaculate effect was observed. A strong time by treatment effect ($P<0.05$) was seen in visual and IVOS motility, as well as in DFI parameters during incubation of conventional sperm. This interaction was not present in sorted sperm.

Figure 22:
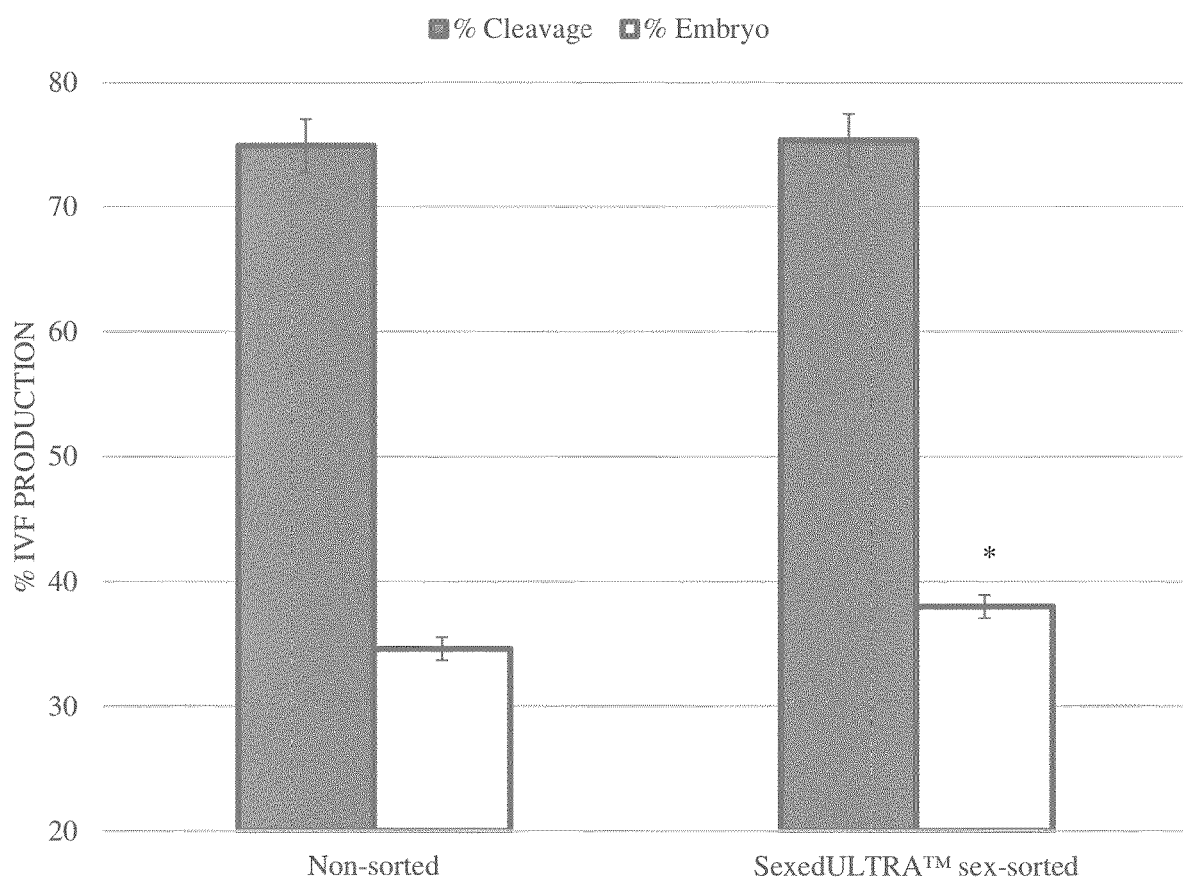
FIG. 22 is a graph showing the increase in IVF embryo production achievable with one embodiment of the invention.

Results from IVF trials are shown in FIG. 22. Percent embryo production was significantly higher ($P<0.05$) when sorted compared with unsorted sperm (37.98±0.92 vs 34.62±0.92).

The results show sperm sorting can clean up morphological issues, improve sperm quality and increase embryo production of low-quality ejaculates by using flow cytometry sorting methods, allowing for ejaculates that would otherwise be discarded, to be processed as bulk-sorted or a sex-sorted product.

What we claim is:

1. A method of processing sperm cells comprising
   a) selecting a population of sperm cells wherein each sperm cell has a cell long axis and wherein greater than 25% of sperm cells in the population have abnormal morphology;
   b) staining the sperm cells in the population;
   c) placing the sperm cells in the population in a channel configured to impart orienting forces on the sperm cells that defines a flow axis and through which the sperm cells flow; wherein the cells, when the cell long axis is parallel with the flow axis, have at least a portion that has a flow orthogonal, cell cross-section that is non-circular, wherein the flow orthogonal, cell cross-section has a flow orthogonal, cell cross-section long axis and a flow orthogonal, cell cross-section short axis that is orthogonal to the flow orthogonal, cell cross-section long axis, wherein the channel configured to impart orienting forces on the sperm cells defines an intended, flow orthogonal, cell cross section long axis alignment line and an intended, flow orthogonal, cell cross section short axis alignment line that is orthogonal to the intended, flow orthogonal, cell cross section long axis alignment line;
   d) orienting cells with the channel such that a cell presented at full orientation during cell irradiation has the cell long axis parallel with the flow axis, the flow orthogonal, cell cross-section long axis aligned with the intended flow orthogonal, cell cross section long axis alignment line; and the flow orthogonal, cell cross-section short axis aligned with the intended, flow orthogonal, cell cross section short axis alignment line;
   e) irradiating the sperm cells in the population with a source of electromagnetic radiation;
   f) detecting fluorescence emitted by the sperm cells in the population using a detector, wherein the detector has a flow orthogonal collection angle that defines a flow orthogonal, detector axis and wherein the flow orthogonal, detector axis is substantially coaxial with the intended, flow orthogonal, cell cross section long axis alignment line; and
   g) creating a gate that excludes a portion of sperm cells in the population, wherein the angle between an excluded cell's flow orthogonal, cell cross-section long axis and the intended, flow orthogonal, cell cross section long axis alignment line is greater than 5°.

2. The method of claim 1, wherein the angle in step g) is greater than 10°.

3. The method of claim 1, wherein the angle in step g) is greater than 15°.

4. A method of processing sperm cells comprising
   a) selecting a population of sperm cells wherein each sperm cell has a cell long axis and wherein greater than 25% of sperm cells in the population have abnormal morphology;
   b) staining the sperm cells in the population;
   c) placing the sperm cells in the population in a channel configured to impart orienting forces on the sperm cells that defines a flow axis and through which the sperm cells flow; wherein the cells, when the cell long axis is parallel with the flow axis, have at least a portion that has a flow orthogonal, cell cross-section that is non-circular, wherein the flow orthogonal, cell cross-section has a flow orthogonal, cell cross-section long axis and a flow orthogonal, cell cross-section short axis that is orthogonal to the flow orthogonal, cell cross-section long axis;
   d) irradiating the sperm cells in the population with a beam of electromagnetic radiation, the beam having a flow orthogonal optical axis;
   e) detecting fluorescence emitted by the sperm cells in the population using a detector, wherein the detector has a flow orthogonal collection angle that defines a flow orthogonal, detector axis and wherein the flow orthogonal, detector axis is orthogonal to the flow orthogonal optical axis; and
   f) creating a gate that excludes a portion of sperm cells in the population, wherein the angle between an excluded cell's flow orthogonal, cell cross-section long axis and the flow orthogonal, detector axis is greater than 5°.

5. The method of claim 4, wherein the angle in step f) is greater than 10°.

6. The method of claim 4, wherein the angle in step f) is greater than 15°.

* * * * *